US012616417B1

(12) United States Patent
Morris et al.

(10) Patent No.: US 12,616,417 B1
(45) Date of Patent: May 5, 2026

(54) METHOD, APPARATUS AND SYSTEM FOR MONITORING HEALTH THROUGH AUDIO DATA

(71) Applicant: Fortell Research Inc., New York, NY (US)

(72) Inventors: Nicholas Morris, Brooklyn, NY (US); Igor Lovchinsky, New York, NY (US); Andrew J. Casper, Inver Grove Heights, MN (US); Matthew de Jonge, Brooklyn, NY (US)

(73) Assignee: Fortell Research Inc., New York, NY (US)

( * ) Notice: Subject to any disclaimer, the term of this patent is extended or adjusted under 35 U.S.C. 154(b) by 470 days.

(21) Appl. No.: 18/100,534

(22) Filed: Jan. 23, 2023

Related U.S. Application Data

(60) Provisional application No. 63/302,474, filed on Jan. 24, 2022.

(51) Int. Cl.
*A61B 5/00* (2006.01)
*G10L 25/30* (2013.01)
(Continued)

(52) U.S. Cl.
CPC .......... *A61B 5/4803* (2013.01); *A61B 5/6815* (2013.01); *A61B 5/7203* (2013.01);
(Continued)

(58) Field of Classification Search
CPC ... A61B 5/4803; A61B 5/6815; A61B 5/7203; A61B 5/7225; A61B 5/7257;
(Continued)

(56) References Cited

U.S. PATENT DOCUMENTS 9,881,631 B2    1/2018  Erdogan et al.
10,721,571 B2   7/2020  Crow et al.
(Continued)

FOREIGN PATENT DOCUMENTS

EP          0 357 212 A2    3/1990
WO      WO 2022/079848 A1    4/2022
(Continued)

OTHER PUBLICATIONS

Giri et al., Personalized Percepnet: Real-time, Low-complexity Target Voice Separation and Enhancement. Amazon Web Service, Jun. 8, 2021, arXiv preprint arXiv:2106.04129. 5 pages.

*Primary Examiner* — Robert J Michaud
(74) *Attorney, Agent, or Firm* — Wolf, Greenfield & Sacks, P.C.

(57) ABSTRACT

According to some embodiments, an ear-worn device, e.g., a hearing aid, is provided that operates to monitor the health of a wearer of the ear-worn device based on an audio signal detected by the ear-worn device. In some embodiments, a method of monitoring the health of the wearer of the ear-worn device includes: detecting the audio signal with a microphone of the ear-worn device; processing the detected audio signal using a processor of the ear-worn device; and outputting, from an output signal generator of the ear-worn device, a generated output audio signal. In some embodiments, processing the detected audio signal includes: extracting data indicative of a health event associated with the wearer by processing the detected audio signal with a machine learning model; generating the output audio signal based on the detected audio signal; and outputting the data indicative of the health event.

66 Claims, 14 Drawing Sheets

(51) Int. Cl.
  G10L 25/66 (2013.01)
  H04R 25/00 (2006.01)
(52) U.S. Cl.
  CPC .......... *A61B 5/7225* (2013.01); *A61B 5/7257* (2013.01); *A61B 5/7282* (2013.01); *G10L 25/30* (2013.01); *G10L 25/66* (2013.01); *H04R 25/00* (2013.01); *A61B 5/0004* (2013.01); *A61B 2562/0204* (2013.01)
(58) Field of Classification Search
  CPC ................ A61B 5/7282; A61B 5/0004; A61B 2562/0204; G10L 25/30; G10L 25/66; H04R 25/00
  See application file for complete search history.

(56) References Cited

U.S. PATENT DOCUMENTS

| 10,812,915 | B2 | 10/2020 | Santos et al. |
| 10,957,301 | B2 | 3/2021 | Hoby et al. |
| 11,330,378 | B1 | 5/2022 | Jelcicováet al. |
| 11,375,325 | B2 | 6/2022 | Froehlich et al. |
| 2020/0253547 | A1 | 8/2020 | Harris et al. |
| 2021/0289299 | A1 | 9/2021 | Durrieu |
| 2022/0095061 | A1 | 3/2022 | Diehl et al. |
| 2022/0159403 | A1 | 5/2022 | Sporer et al. |
| 2022/0223161 | A1 | 7/2022 | Fuchs et al. |
| 2022/0230048 | A1 | 7/2022 | Li et al. |
| 2022/0232321 | A1* | 7/2022 | Wexler ................ G10L 21/0216 |
| 2022/0232331 | A1 | 7/2022 | Jelcicováet al. |
| 2022/0256294 | A1 | 8/2022 | Diehl et al. |
| 2023/0104773 | A1* | 4/2023 | Gurin ....................... A61B 5/01 |
| | | | 600/549 |

FOREIGN PATENT DOCUMENTS

| WO | WO 2022/107393 | A1 | 5/2022 |
| WO | WO 2022/191879 | A1 | 9/2022 |

* cited by examiner

METHOD, APPARATUS AND SYSTEM FOR MONITORING HEALTH THROUGH AUDIO DATA

CROSS-REFERENCE TO RELATED APPLICATIONS

This application claims the benefit under 35 U.S.C. § 119(e) of U.S. Provisional Application Ser. No. 63/302,474, filed Jan. 24, 2022, and entitled "METHOD, APPARATUS AND SYSTEM FOR MONITORING HEALTH THROUGH AUDIO DATA", which is hereby incorporated by reference herein in its entirety.

BACKGROUND

The present application relates to ear-worn devices, such as hearing aids. Hearing aids are used to help those who have trouble hearing to hear better. They are typically positioned in, or near, the ear.

BRIEF SUMMARY

According to some embodiments, a method of monitoring health of a wearer of an ear-worn device based on an audio signal detected by the ear-worn device is provided. The method comprises: detecting the audio signal with a microphone of the ear-worn device; processing the detected audio signal using a processor of the ear-worn device, the processing comprising: extracting data indicative of a health event associated with the wearer of the ear-worn device by processing the detected audio signal with a machine learning model; generating an output audio signal based on the detected audio signal; and outputting the data indicative of the health event associated with the wearer of the ear-worn device; and outputting, from an output signal generator of the ear-worn device, the generated output audio signal.

According to some embodiments, an ear-worn device is provided. The ear-worn device is configured to monitor health of a wearer of the ear-worn device based on an audio signal detected by the ear-worn device. The ear-worn device comprises: a microphone configured to detect the audio signal; a processor; at least one non-transitory computer-readable storage medium storing processor-executable instructions that, when executed by the processor, cause the processor to perform a method comprising: extracting data indicative of a health event associated with the wearer of the ear-worn device by processing the detected audio signal with a machine learning model; generating an output audio signal based on the detected audio signal; and outputting the data indicative of the health event associated with the wearer of the ear-worn device; and an output signal generator configured to output the generated output audio signal.

According to some embodiments, at least one non-transitory computer-readable storage medium storing processor-executable instructions that, when executed by a processor, cause the processor to perform a method of monitoring health of a wearer of an ear-worn device based on an audio signal detected by the ear-worn device is provided. The method comprises: extracting data indicative of a health event associated with the wearer of the ear-worn device by processing the detected audio signal with a machine learning model to extract data indicative of a health event associated with the wearer of the ear-worn device; generating an output audio signal based on the detected audio signal; outputting the data indicative of the health event associated with the wearer of the ear-worn device; and transmitting the output audio signal to an output signal generator of the ear-worn device.

BRIEF DESCRIPTION OF DRAWINGS

Various aspects of the application will be described with reference to the following figures. It should be appreciated that the figures are not necessarily drawn to scale. Items appearing in multiple figures are indicated by the same reference number in all the figures in which they appear.

DETAILED DESCRIPTION

Figure 1:
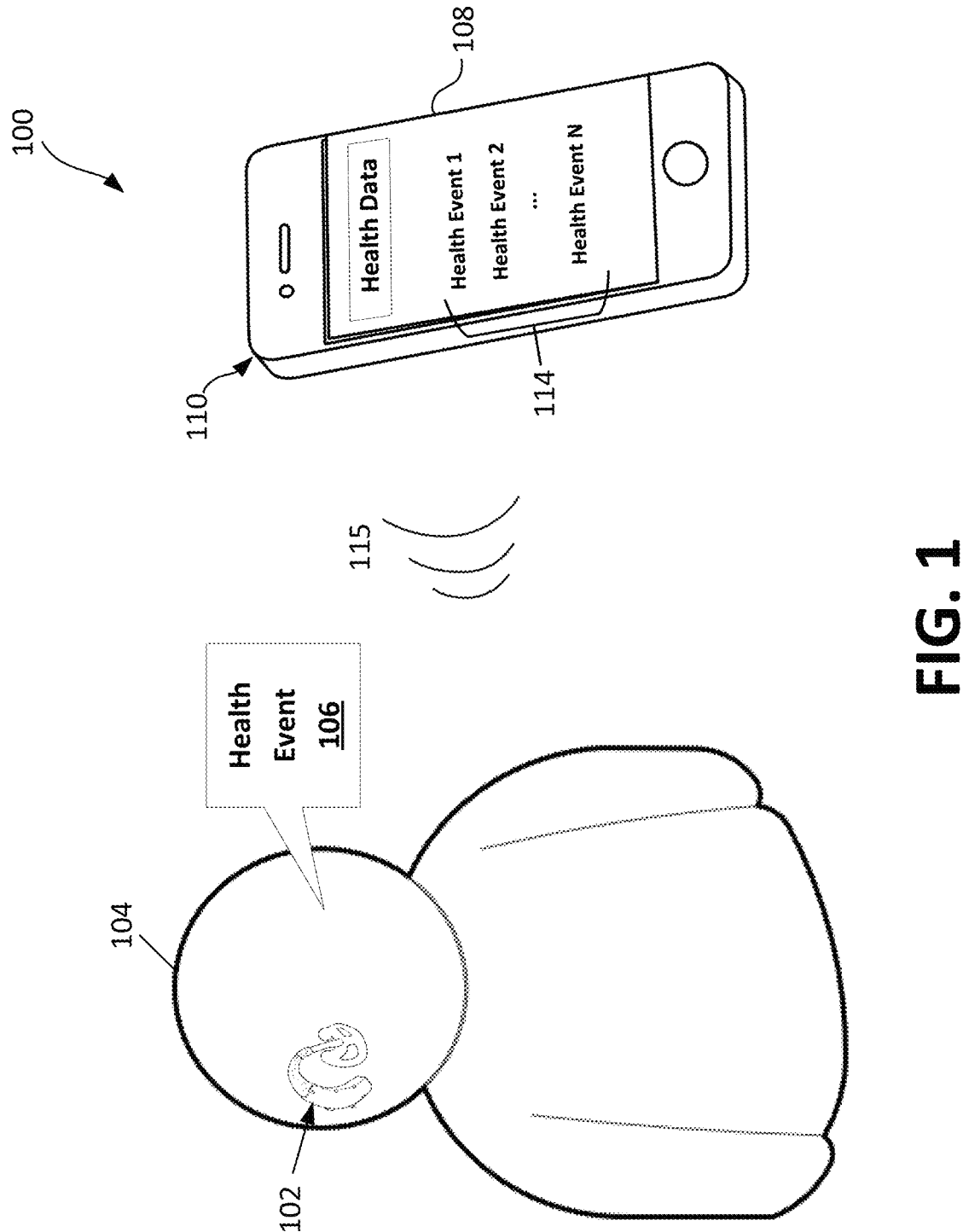
FIG. 1 illustrates detection of a health event using an ear-worn device, according to a non-limiting embodiment of the present application.

According to an aspect of the technology described herein, an ear-worn device, which is a hearing aid in at least some embodiments, is provided that operates to monitor the health of the person wearing the ear-worn device. The ear-worn device includes a processor, a microphone coupled to the processor, and an output signal generator coupled to the processor. The ear-worn device may operate by detecting an audio signal with the microphone, processing the detected audio signal using the processor to generate an output audio signal based on the detected audio signal, and outputting, from an output signal generator of the ear-worn device, the generated output audio signal. These steps may produce an audible signal for the wearer that is enhanced compared to the audio signal detected by the microphone. Additionally, processing the detected audio signal using the processor further includes extracting data indicative of a health event associated with the wearer of the ear-worn device by processing the detected audio signal with a machine learning model. The ear-worn device may further output the data indicative of the health event associated with the wearer of the ear-worn device. In some embodiments, the data indicative of the health event is used to determine whether to trigger a health intervention.

Thus, it should be appreciated that according to an aspect of the present technology, a dual-function hearing aid is provided. The hearing aid both enhances incoming sound to provide the wearer with an enhanced audio signal and analyzes the incoming sound to detect characteristics of the sound that indicate something about the health of the person wearing the hearing aid. Therefore, the incoming sound is processed by the hearing aid for two purposes. Any information determined from the incoming sound to be indicative of the health of the wearer may be provided to a remote device, such as a smartphone or computer, for further analysis and/or action.

Collecting and interpreting data is an important aspect of a healthcare regimen. For example, practitioners interacting with patients routinely collect vital signs from patients including weight, temperature, heart rate, and blood pressure. Practitioners also collect responses to standard questions (e.g., questions regarding mental state) and/or qualitative results of a routine physical exam. However, such data is typically only collected at the time of the visit, capturing only a snapshot in time.

Some sensing devices collect data during times outside of a patient's visit with a healthcare provider. For example, patients with diabetes can use continuous glucose monitors to track their blood sugar level. Additionally, some devices (e.g., smartphones, smart watches, etc.) can be used to monitor heart rate, temperature, and levels of activity. By capturing data over time, a user or their healthcare provider has access to more information with which to assess the patient's health.

The inventors have recognized that audio data can be an important source of information for monitoring the health of a patient. For example, coughing and wheezing may indicate that the patient has a respiratory condition. A characteristic of a cough (e.g., wetness, frequency, etc.) may be indicative of a specific type of respiratory condition. As another example, characteristics of a patient's snoring or breathing may indicate that the patient has sleep apnea or another sleep condition. As yet another example, the tone and/or frequency of the patient's speech or conversation with others may provide insight into the patient's mental state. The fact that a person may stop socializing with others could be indicative of a decrease in activity or deteriorating mental health. Most, if not all, of this audio data cannot be collected during one or more healthcare visits.

While audio data can be valuable for monitoring the health of a patient, conventional techniques for continuously monitoring aspects of patient's health are not equipped to reliably monitor audio data and detect health events. In particular, conventional health monitoring devices such as smart watches, blood glucose monitors, and fitness trackers) are not tailored for acquiring and processing high quality audio data as would be a hearing aid. Without high quality audio data, it is challenging to distinguish health events (e.g., coughs, breathing, snores, drinking, etc.) from background noise. Accordingly, such devices cannot be used to reliably extract health data from any audio data collected using such devices.

Hearing aids, on the other hand, may be tailored to the collection and processing of high-quality audio since their primary purpose is to provide enhanced hearing for the wearer. Hearing aids may include circuitry specifically tailored to the functions of collecting and analyzing audio signals for purposes of producing enhanced audio for the wearer. Additionally, hearing aids may be worn in or near the ear, positioned differently than other devices that collect data such as smartphones, glucose monitors, and fitness trackers. Thus, hearing aids may collect data that more accurately reflects what the wearer hears, and the nature of sounds close to the wearer's ears, such as sounds from the wearer's mouth and/or nose.

Conventional hearing aids lack the ability to handle the computational complexity of extracting key information from audio data for monitoring health. Machine learning and neural network may be used to reliably classify sounds. For continuous processing, neural networks can require orders of magnitude more operations than the typical signal chain that runs on a conventional hearing aid. Conventional hearing aids are constrained by small size and battery life.

The inventors have developed methods and apparatus that address the above-described challenges of conventional health monitoring techniques. In some embodiments, an ear-worn device is provided that is configured to monitor the health of a wearer of the ear-worn device using audio data detected by the ear-worn device. In some embodiments, the ear-worn device is a hearing aid. An advantage of monitoring health with a hearing aid is that a high percentage of elderly people, a common demographic for which it is desirable to monitor health on a regular basis outside of medical appointments, already wear a hearing aid. Accordingly, those individuals would not need to make an additional purchase, wear an additional device, or learn how to use a new technology. Another advantage of monitoring health with a hearing aid is that when they are worn in or near the ear they are located near sources of sound that may be of interest for monitoring health events, allowing for the collection of high-quality audio data relating to such events. For example, given the proximity of the ear to the nose and mouth, high quality audio data of events such as coughing, speaking, wheezing, snoring, and other similar sounds may be collected. Yet another advantage of monitoring health with a hearing aid is that the same circuitry that is used to process the input audio signal for purposes of producing an enhanced output audio signal for the wearer may also be used to process the incoming audio signal to detect health-related events reflected in the audio signal, thereby enabling health monitoring without compromising important features of the hearing aid, such as size and battery.

In some embodiments of the present technology, the techniques for monitoring the health of a wearer of an ear-worn device (e.g., a hearing aid) include processing an audio signal detected by a microphone of the ear-worn device to both (a) generate an output audio signal, and (b) extract data indicative of a health event. Generating the output audio signal may include enhancing the incoming audio signal based on the needs of the wearer. For example, this may include removing a noise component of the detected audio signal and/or increasing a volume of the incoming audio signal. The signal-to-noise ratio (SNR) may be increased compared to the detected audio signal. Extracting the data indicative of the health event may include processing the detected audio signal to detect coughing, speaking, talking, wheezing, snoring, chewing, swallowing, or any other suitable data indicative of an audible health event. Accordingly, in some embodiments, the ear-worn device operates not only to enhance audio data to address the hearing needs of the wearer, but also uses that same audio data to monitor the health of the wearer.

In some embodiments, extracting data indicative of a health event includes one or both of (a) detecting the health event, and (b) characterizing the health event. For example, detecting a health event may include detecting the occurrence of a health event. When a health event has been detected, characterizing the health event may include determining a type of health event (e.g., a cough versus a snore) and/or, more specifically, a characteristic of the type of the detected health event (e.g., wetness of a cough).

In some embodiments, detecting and/or characterizing a health event may be performed by processing audio data detected by an ear-worn device with one or more machine learning models. For example, a health event detector machine learning model may be trained to predict, based on a segment of audio data, whether the segment of audio data includes a component attributable to a health event. This may include distinguishing between different sources of sound, such as background noise, speech, and/or health events. In some embodiments, a health event characterization machine learning model may be trained to process a segment of audio data, which includes a component attributable to a health event, to characterize the health event. For example, the health event characterization machine learning model may be trained to distinguish between different types of health events. As an additional, or alternative example, the health event characterization machine model may be trained to distinguish between different types of coughs, such as wet coughs and dry coughs. In some embodiments, the health event characterization machine learning model may be larger and/or more complex that the health event detector machine learning model.

In some embodiments, audio data indicative of one or more health events can be collected and used to monitor the health of the wearer over time. For example, increased frequency of coughing events may indicate the worsening of a respiratory condition. In some embodiments, if the data satisfies health criteria (e.g., the frequency of coughs exceeds a threshold frequency), then the techniques may include triggering a health intervention. For example, a recommendation may be output to a wearer of the ear-worn device to schedule an appointment with a clinician, a recommendation may be output to a clinician to treat the wearer of the ear-worn device, and/or a health intervention may be administered by the clinician.

The aspects and embodiments described above, as well as additional aspects and embodiments, are described further below. These aspects and/or embodiments may be used individually, all together, or in any combination of two or more, as the disclosure is not limited in this respect.

FIG. 1 illustrates detection of a health event using an ear-worn device, according to a non-limiting embodiment of the present technology. As shown in FIG. 1, an audio system 100 includes an ear-worn device 102 and a separate electronic device 110. In this example, the ear-worn device is a hearing aid and the electronic device 110 is a smartphone. Other types of electronic devices may be used, such as tablet computers or laptop computers, as non-limiting examples.

In some embodiments, the ear-worn device 102 detects sounds and outputs an audio signal to the ear-worn device wearer 104. For example, the ear-worn device wearer may be hard of hearing, and the ear-worn device 102 may be a hearing aid. The ear-worn device 102 may process the detected sound to address the hearing needs of the wearer 104. For example, the ear-worn device 102 may process the sounds to suppress noise and/or enhance speech of one or more speakers. The enhanced audio signal may be output to the wearer 104 via a speaker device.

Additionally, or alternatively, the ear-worn device 102 detects sounds and outputs data indicative of a health event 106. For example, the data indicative of the health event 106 may include an isolated component of the sound associated with the health event 106 and/or data indicative of a characterization of the health event 106. For example, the ear-worn device may process one or more components of the detected sound with a machine learning model to obtain an output indicative of a characterization of the sound.

The ear-worn device 102 and electronic device 110 may work in combination to monitor the health of the wearer 104. For example, the electronic device 110 may receive from the ear-worn device 102 data indicative of a health event. The electronic device 110 may store the received data and/or be configured to process the received data. For example, after receiving data indicative of multiple health events (e.g., health events 1 through N 114), the electronic device 110 may be configured to evaluate the data to determine a trend in the wearer's health over time.

In some embodiments, the electronic device 110 is additionally, or alternatively, configured to transmit data indicative of one or more health events to a server and/or store such data in one or more data store(s). Accordingly, in some embodiments, the data on the server and/or stored in the data store(s) can be accessed by other computing devices. For example, such data may be accessed by a clinician using a computing device at a remote healthcare facility.

The electronic device 110 includes a display screen 108 which displays health events 114 based on data received from the ear-worn device 102. The ear-worn device wearer can interact with the display screen 108 to self-monitor their health via the health events 114. Additionally, or alternatively, the display screen may display metric(s) determined based on the data indicative of the health events and/or recommendation(s) for health intervention(s).

The ear-worn device 102 and electronic device 110 may communicate via a wireless or wired link. In the example of FIG. 1, the ear-worn device and electronic device communicate via a wireless link 115.

Figure 2:
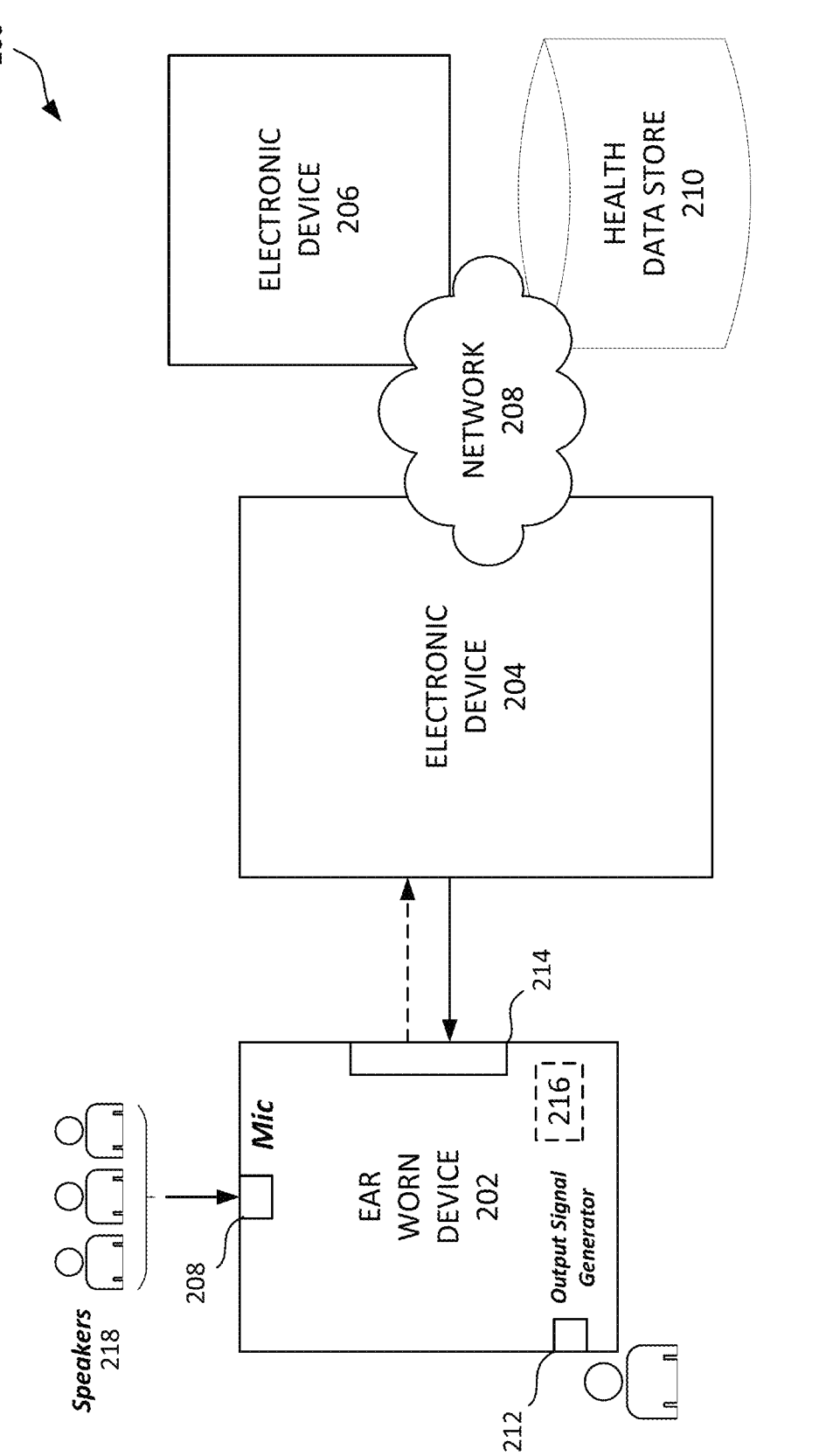
FIG. 2 illustrates a system with an ear-worn device and a portable electronic device for monitoring the health of a wearer of an ear-worn device, according to a non-limiting embodiment of the present application.

FIG. 2 illustrates a system with an ear-worn device and a portable electronic device for monitoring the health of a wearer of an ear-worn device, according to a non-limiting embodiment of the present application. Audio system 200 may be an example implementation of the system shown in FIG. 1. For example, audio system 200 may include an ear-worn device 202 and electronic device 204. The ear-worn device 202 may be an example implementation of the ear-worn device 102 of FIG. 1. Ear-worn device 202 as described in FIG. 2 may have various forms. For example, the ear-worn device may be a hearing aid or a headphone, or any suitable audio device worn in or on the ear. Additionally, ear-worn device 202 may include a communication port 214 configured to communicate (e.g., wired or wirelessly) with an external device and exchange data with an external device, such as electronic device 204. Electronic device 204 may be an example implementation of the electronic device 110 of FIG. 1. For example, electronic device 204 may be a smart phone, or any suitable portable electronic device associated with the wearer of the ear-worn device.

In some non-limiting examples, ear-worn device 202 may include a microphone ("mic") 208 and an output signal generator (e.g., a speaker device) 212. Microphone 208 may be configured to detect audio signal from sound (e.g., speech). For example, the audio signal may include speech components from one or more speakers 218. The detected audio signal may also include environment noise, such as music, wind, a car horn, or other sounds in the environment. Ear-worn device 202 may be capable of processing the audio signal detected by the microphone 208 to generate an audio signal according to preferences and/or hearing needs of the wearer.

Figure 3A:
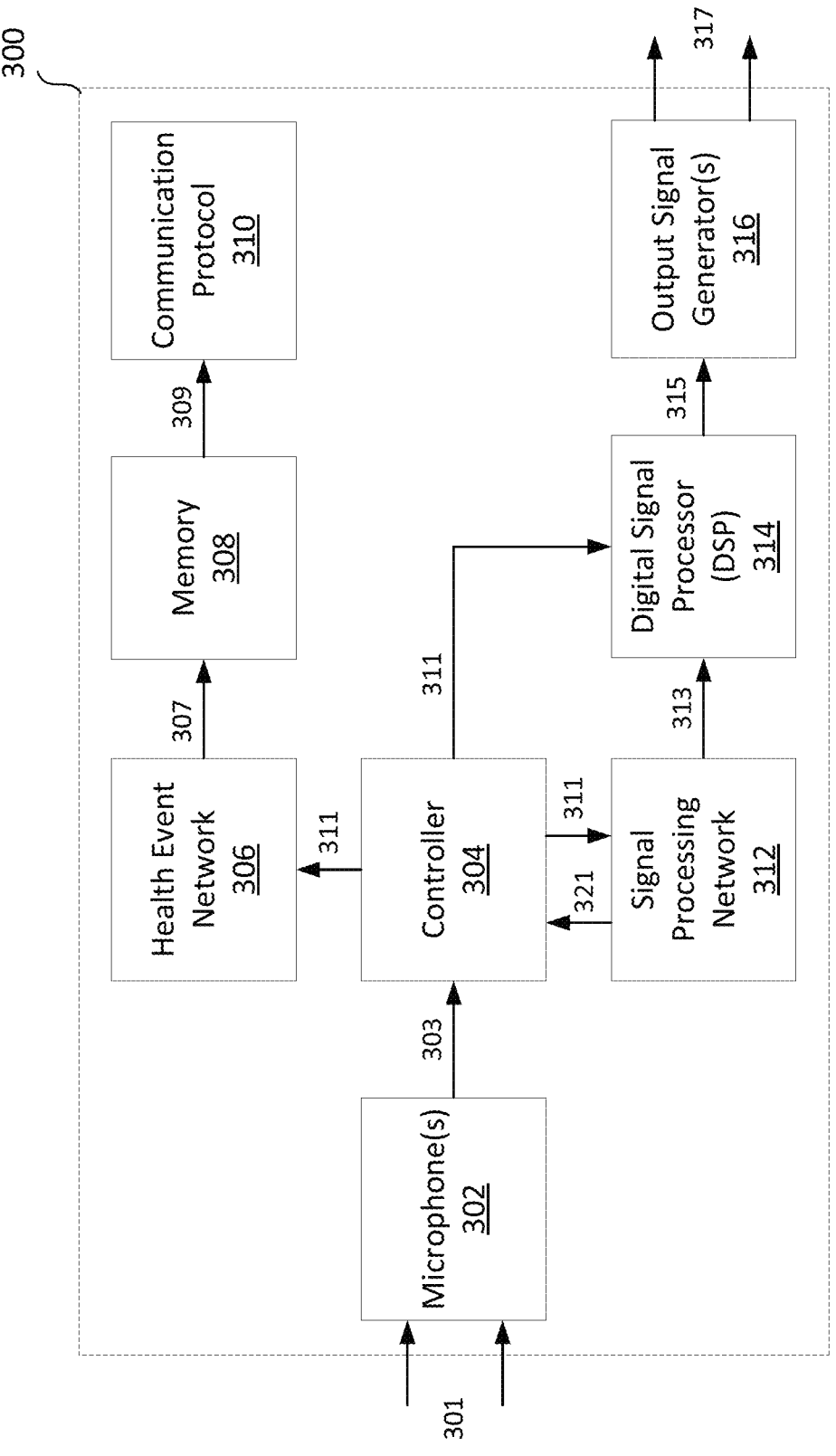
FIG. 3A illustrates example components of an ear-worn device that may be configured to detect a health event of a wearer of the ear-worn device, according to a non-limiting embodiment of the present application.

FIG. 3A illustrates example components of an ear-worn device that may be configured to detect a health event of a wearer of the ear-worn device and/or used to enhance audio signals detected by the ear-worn device, according to a non-limiting embodiment of the present application. In some embodiments, ear-worn device 300 may be an implementation of at least a portion of the ear-worn device 102 of FIG. 1 and 202 of FIG. 2. Ear-worn device 300 may include one or more microphones 302, controller 304, health event network 306, memory 308, communication protocol circuit 310, signal processing network 312, digital signal processor (DSP, 314), and one or more output signal generator(s) 316.

In some embodiments, microphone(s) 302 may be configured to detect an audio signal. The audio signal may be generated by the microphone(s) from sound 301, e.g., speech in a conversation. In a multi-speaker conversation, the audio signal detected by the microphone(s) may include speech components attributable to multiple speakers. In some embodiments, the audio signal detected by the microphone(s) may be analog signal. The ear-worn device 300 may additionally include an analog-to-digital converter (ADC, not shown) to convert the analog signal to digital signal 303 as input to the controller 304. In some embodiments, the microphone(s) 302 may be capable of producing digital audio signals. In such case, the audio signal detected by the microphone(s) may be digital signal 303, which can be directly provided to the controller 304.

Controller 304 receives digital audio signal 303 from microphone(s) 302. Controller 304 may comprise one or more processor circuits (herein, processors), memory circuits and other electronic and software components configured to, among others, (a) perform digital signal processing manipulations necessary to prepare the signal for processing by the signal processing network 312, the DSP 314, and/or the health event network 306, and (b) to determine the next step in the processing chain from among several options. In one embodiment of the disclosure, controller 304 executes a decision logic to determine whether to advance signal processing through one or both of DSP 314 and signal processing network 312. For example, DSP 314 may be activated at all times, whereas controller 304 executes decision logic to determine whether to activate the signal processing network 312 or bypass the signal processing network by deactivating the signal processing network 312. Additionally, or alternatively, in some embodiments, controller 304 executes decision logic to determine whether to advance the signal to health event network 306.

Signal processing network 312 may comprise one or more actual and virtual circuits to receive controller output signal 311 and provide enhanced digital signal 313. In an exemplary embodiment, signal processing network 312 enhances the signal by using a neural network algorithm (NN model) to generate a set of intermediate signals. Each intermediate signal is a representative of one or more of the original sound sources that constitute the original signal. For example, incoming signal 301 may comprise of two speakers, an alarm and other background noise. In some embodiments, the NN model executed on signal processing network 312 may generate a first intermediate signal representing the speech and a second intermediate signal representing the background noise. Signal processing network 312 may also isolate one of the speakers from the other speaker. Signal processing network 312 may isolate the alarm from the remaining background noise to ensure that the user hears the alarm even when the noise-canceling mode is activated. Different situations may require different intermediate signals and different embodiments may contain different neural networks with different capabilities best suited to the wearer's needs. In certain embodiments, a remote (off-chip) signal processing network may augment the capability of the local (on-chip) signal processing network. A signal processing network may include a neural network engine (NNE), such as a recurrent NNE. Examples of neural network engines are described in U.S. patent application Ser. No. 17/576,718, which is incorporated by reference herein in its entirety.

In some embodiments, DSP 314 may be configured to apply a set of filters to the incoming audio components. Each filter may isolate incoming signals in a desired frequency range and apply a non-linear, time-varying gain to each filtered signal. The gain value may be set to achieve dynamic range compression or may identify stationary background noise. DSP 314 may then recombine the filtered and gained signals to provide an output signal 315.

Output signal generator(s) 316 may be configured to output the digital audio signal 317 for playback to the wearer of the ear-worn device. For example, the output signal generator(s) 316 may receive digital signal 315 from the DSP 314 and convert the digital signal 315 to analog signal before producing the output signal 317. In other examples, the ear-worn device may additionally include a digital-to-analog converter (DAC, not shown) to convert the digital signal 315 to analog signal as input to the output signal generator(s) 316 for providing the output signal 317.

Health event network 306 may comprise one or more actual and virtual circuits to receive and process controller output signal 311 to generate output 307. The output 307 may be indicative of whether signal component(s) of the incoming audio signal 301 are attributable to a health event. Additionally, or alternatively, when a health event has been detected, the output 307 may be indicative of a type of health event (e.g., coughing, sneezing, wheezing, swallowing, chewing, breathing, speech, etc.), and/or a characterization of a health event (e.g., a level of wetness or dryness of a cough). In an exemplary embodiment, health event network 306 processes the signal 311 by using one or more neural network algorithms (NN model) to generate the output 307. For example, the health event network 306 may process the signal with a first neural network algorithm configured to detect the presence of a health event. If a health event is detected using the first neural network, the health event network 306 may process the signal with a second neural network to determine the type and/or characterization of the health event. If a health event is not detected with the first neural network, then processing at the health event network 306 may end. In certain embodiments, a remote (off-chip) health event network may augment the capability of the local (on-chip) health event network. A health event network may include a neural network engine (NNE), such as a recurrent NNE. One advantage of using a recurrent NNE is that it can be computed efficiently on an application-specific integrated circuit (ASIC) designed for a recurrent NNE.

In some embodiments, health event network 306 transmits output 307 to memory 308. Memory 308 may be configured to store health event data (e.g., output 307). For example, the health event data may include an indication of the occurrence of a health event, an audio clip of the health event, a type of the health event, a characterization of the health event, and/or any other suitable data.

In some embodiments, communication protocol circuit 310 configured to communicate (e.g., wired or wirelessly) with an external device and exchange data with an external device. For example, communication protocol circuit 310 may receive data 309, such as health event data, from memory 308 and transmit the received data to an external device. In some embodiments, the communication protocol circuit 310 is configured to sync health event data to an external electronic device at regular or irregular intervals. Communication protocol circuit 310 may be an implementation of communication port 214 in FIG. 2

As stated, in one embodiment, the controller performs digital signal processing operations to prepare the signal for processing by one or more of DSP 314, signal processing network 312, and health event network 306. Signal processing network 312, health event network 306, and DSP 314 may accept as input the signal in the time-frequency domain (e.g., signal 311), so that controller 304 may take a Short-Time Fourier Transform (STFT) of the incoming signal before passing it onto signal processing network 312, health event network 306, or DSP 314. In another example, controller 304 may perform beamforming of signals received at different microphones to enhance the audio signals coming from certain directions.

In some embodiments, the controller 304 continually determines the next step in the signal processing chain for processing the received audio data. The signal processing chain of ear-worn device 300 may include two branches. In some embodiments, an audio enhancement branch may be configured to enhance the received audio data and generate output signal 317. For example, the audio enhancement branch may include the signal processing network 312, the DSP 314, and/or the output signal generator(s) 316. In some embodiments, a health monitoring branch may be configured to detect, classify, and/or characterize health events, store health event data, and/or transmit health event data to external electronic device(s). For example, the health monitoring branch may include the health event network 306, memory 308, and communication protocol circuit 310.

In some embodiments, in determining the next step in the signal processing chain, the controller 304 determines whether to transmit controller output signal to one or both of the signal processing branch and the health monitoring branch. Additionally, or alternatively, the controller may be configured to determine the next step in a particular branch in the signal processing chain for processing the received audio data. For example, as described herein in more detail, within the audio enhancement branch, the controller 304 may determine whether controller output signal 311 is to be transmitted to one or both of the signal processing network 312 and the DSP 314.

In certain embodiments, controller 304 continually determines the next step in the signal chain for processing the received audio data to generate output signal 317. For example, controller 304 activates signal processing network 312 based on one or more of user-controlled criteria, user-agnostic criteria, user clinical criteria, accelerometer data, location information, stored data and the computed metrics characterizing the acoustic environment, such as SNR. For example, in response to a determination that the speech is continual, or that the SNR of the input audio signal is above a threshold ratio, controller 304 may activate the signal processing network 312. Otherwise, controller 304 may deactivate the signal processing network 312, leaving the DSP 314 activated. This results in a power saving of the ear-worn device when the signal processing network 312 is not needed. If signal processing network 312 is not activated, controller 304 instead passes signal 311 directly to DSP 314. In some embodiments, controller 304 may pass data to both the signal processing network 312 and DSP 314 simultaneously as indicated by arrows from controller 304 to DSP 314 and to signal processing network 312.

In some embodiments, user-controlled criteria may represent one or more logics (e.g., hardware- or software-implemented). In some examples, user-controlled criteria may comprise user inputs including the selection of an operating mode through an application on a user's smartphone or input on the ear-worn device (for example by the wearer of the ear-worn device tapping the device). For example, when a user is at a restaurant, she may change the operating mode to noise cancellation/speech isolation by making an appropriate selection on her smartphone. Additionally, and/or alternatively, user-controlled criteria may comprise a set of user-defined settings and preferences which may be either input by the user through an applet or an application (app) or learned by the device over time. For example, user-controlled criteria may comprise a user's preferences around what sounds the wearer of the ear-worn device hears (e.g., new parents may want to always amplify a baby's cry, or a dog owner may want to always amplify barking) or the user's general tolerance for background noise. Additionally, and/or alternatively, user clinical criteria may comprise a clinically relevant hearing profile, including, for example, the user's general degree of hearing loss and the user's ability to comprehend speech in the presence of noise.

User-controlled logic may also be used in connection with or aside from user-agnostic criteria (or logic). User-agnostic logic may consider variables that are independent of the user. For example, the user-agnostic logic may consider the hearing aid's available power level, the time of day, or the expected duration of the signal processing network 312 operation (as a function of the anticipated signal processing network execution demands).

In some embodiments, acceleration data as captured on sensors in the device may be used by controller 304 in determining whether to direct signal controller output signal 311 to one or both of DSP 314 and signal processing network 312. Movement or acceleration information may be used by controller 304 to determine whether the user is in motion or sedentary. Acceleration data may be used in conjunction with other information or may be overwritten by other data. Similarly, data from sensors capturing acceleration may be provided to the signal processing network as information for inference.

In other embodiments, the user's location may be used by controller 304 to determine whether to engage one or both of DSP 314 and signal processing network 312. Certain locations may require activation of signal processing network 312. For example, if the user's location indicates high ambient noise (e.g., the user is strolling through a park or is attending a concert) and no direct conversation, controller 304 may activate DSP 314 only and deactivate signal processing network 312. On the other hand, if the user's location suggests that the user is traveling (e.g., via car or train) and other indicators suggest human communication, then controller 304 may activate signal processing network 312 to enhance the audio signal by amplifying human voices over the surrounding noise.

In some embodiments, controller 304 may execute an algorithmic logic to select a processing path. For example, controller 304 may detect SNR of input audio signal 303 and determine whether one or both of DSP 314 and signal processing network 312 should be engaged. In one implementation, controller 304 compares the detected SNR value with a threshold value and determines which processing path to initiate. The threshold value may be one or more of empirically determined, user-agnostic or user-controlled. Controller 304 may also consider other user preferences and parameters in determining the threshold value as discussed above.

In another embodiment, controller 304 may compute certain metrics to characterize the incoming audio as input for determining a subsequent processing path. These metrics may be computed based on the received audio signal. For example, controller 304 may detect periods of silence, knowing that silence does not require the signal processing network to enhance, and it should therefore deactivate the signal processing network. In another example, controller 304 may include a Voice Activity Detector (VAD) to determine the processing path in a speech-isolation mode. In some embodiments, the VAD may be a compact (e.g., much less computationally intensive) neural network in the controller.

In an exemplary embodiment, controller 304 may receive the output of the signal processing network 312 for recently processed audio, as indicated by arrow 321 from signal processing network 312 to controller 304, as input to controller 304. Signal processing network 312, which may be configured to isolate target audio in the presence of background noise, provides the inputs necessary to robustly estimate the SNR. Controller 304 may in turn use the output of the signal processing network 312 to detect when the SNR of the incoming signal is high enough or too low to influence the processing path. In still another example, the output of signal processing network 312 may be used to improve the robustness of VAD. Voice detection in the presence of noise is computationally intensive. By leveraging the output of signal processing network 312, ear-worn device 300 can implement this task with minimal computation overhead when the noise is suppressed based on isolated speech from the NNE.

When controller 304 utilizes signal processing network output 321, it can only utilize the output to influence the signal path for subsequently received audio signal. When a given sample of audio signal is received at the controller, the output of signal processing network 312 for that sample will be computed with a delay, where the output of the signal processing network, if computed before the next sample arrives, will influence the controller decision for the next sample. When the time interval of the sample is small enough, e.g., a few milliseconds or less than a second, such delay will not be noticeable by the wearer.

When signal processing network 312 is activated, using the output 321 of the signal processing network 312 in the controller does not incur any additional computational cost. In certain embodiments, controller 304 may engage signal processing network 312 for supportive computation even in a mode when signal processing network 312 is not the selected signal path. In such a mode, incoming audio signal is passed directly from controller 304 to DSP 314 but data (i.e., audio clips) is additionally passed at less frequent intervals to signal processing network 312 for computation. This computation may provide an estimate of the SNR of the surrounding environment or detect speech in the presence of noise in substantially real time.

Figure 3B:
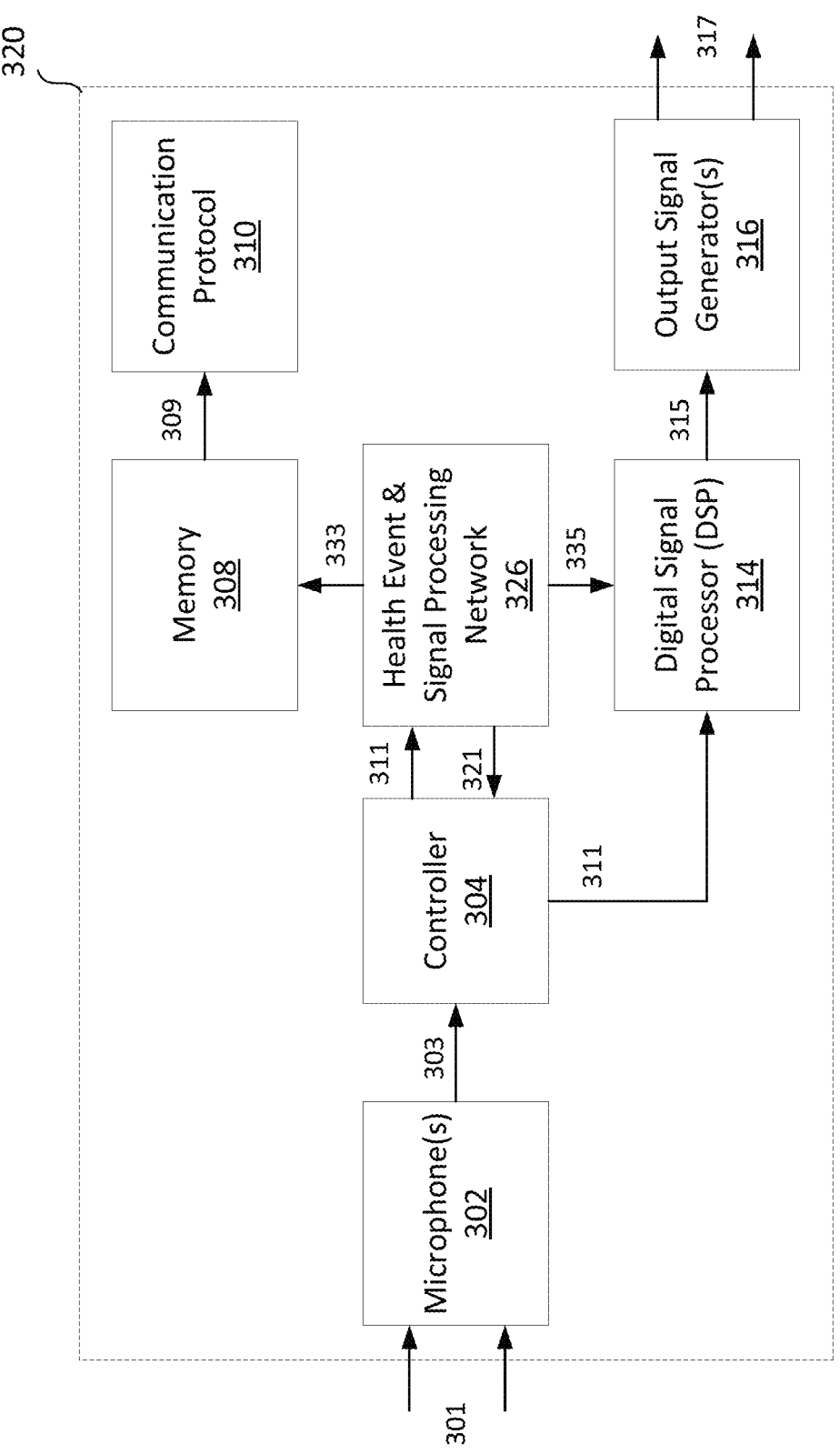
FIG. 3B illustrates example components of a variation of the ear-worn device of FIG. 3A that may be configured to detect a heath event of a wearer of the ear-worn device, according to a non-limiting embodiment of the present application.

FIG. 3B illustrates example components of a variation of the ear-worn device of FIG. 3A that may be configured to detect a heath event of a wearer of the ear-worn device, according to a non-limiting embodiment of the present application. In some embodiments, ear-worn device 320 may be an implementation of at least a portion of the ear-worn device 102 of FIG. 1, 202 of FIG. 2, and 300 of FIG. 3A. Similar to FIG. 3A, ear-worn device includes one or more microphones 302, controller 304, DSP 314, output signal generator(s) 316, memory 308, and communication protocol circuit 310. However, ear-worn device 320 differs from the ear-worn device 300 in that it includes health event and signal processing network 326.

In some embodiments, health event and signal processing network 326 is configured to perform the tasks of both the signal processing network 312 and the health event network 306 in FIG. 3A. Health event and signal processing network 326 may comprise one or more actual and virtual circuits to receive and process controller output signal 311 to generate output signal 333 and output signal 335. In an exemplary embodiment, health event and signal processing network 326 enhances the audio signal by using a neural network algorithm (NN model) to generate a set of intermediate signals and/or to isolate target sounds. The health event and signal processing network 326 additionally, or alternatively, processes the signal 311 by using one or more neural network algorithms (NN model) to detect, classify, and/or characterize audible health events present in incoming signal 301. In some embodiments, the output signal 333 comprises an enhanced audio signal, while the output signal 335 comprises data indicative of a health event. In certain embodiments, a remote (off-chip) health event and signal processing network may augment the capability of the local (on-chip) health event and signal processing network. A health event and signal processing network may include a neural network engine (NNE), such as a recurrent NNE.

Figure 3C:
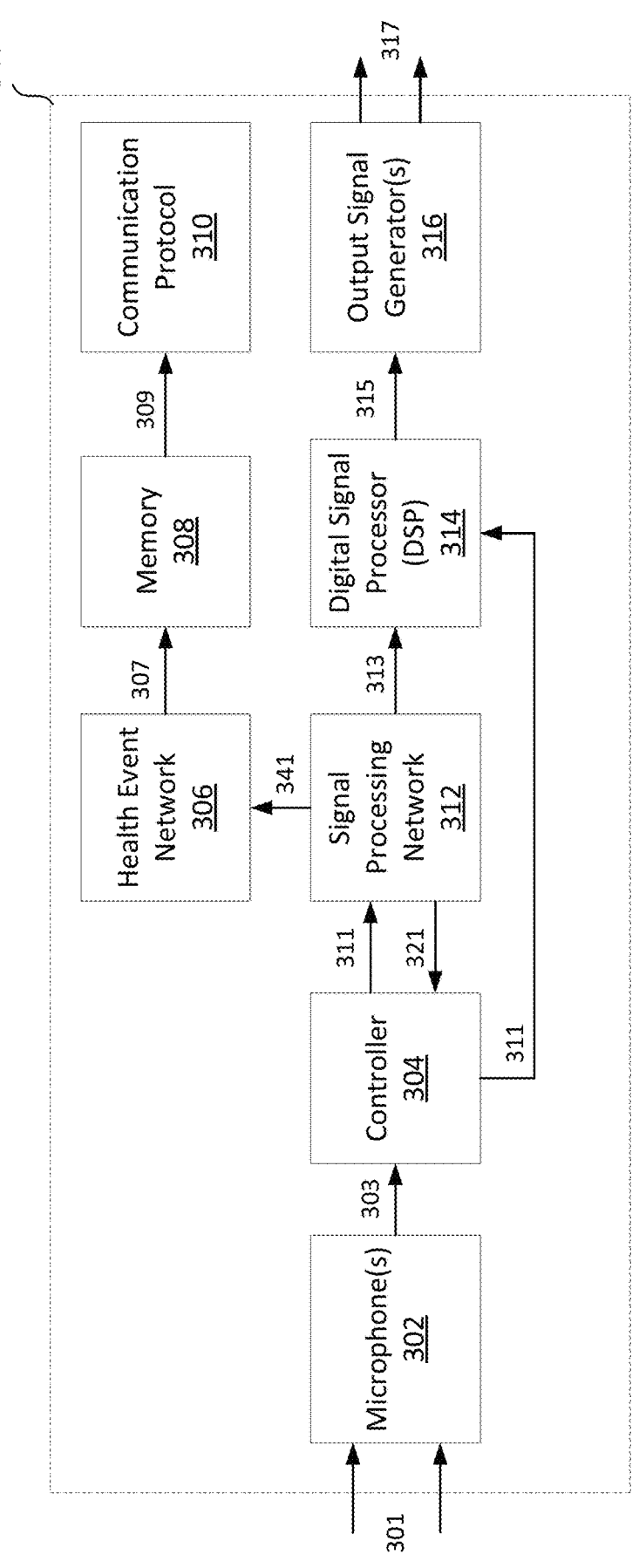
FIG. 3C illustrates example components of a variation of the ear-worn device of FIG. 3A that may be configured to detect a health event of a wearer of the ear-worn device, according to a non-limiting embodiment of the present application.

FIG. 3C illustrates example components of a variation of the ear-worn device of FIG. 3A that may be configured to detect a health event of a wearer of the ear-worn device, according to a non-limiting embodiment of the present application. In some embodiments, ear-worn device 340 may be an implementation of at least a portion of the ear-worn device 102 of FIG. 1, 202 of FIG. 2, 300 of FIG. 3A, and 320 of FIG. 3B. Similar to FIG. 3A, ear-worn device includes one or more microphones 302, controller 304, signal processing network 312, DSP 314, output signal generator(s) 316, health event network 306, memory 308, and communication protocol circuit 310. However, ear-worn device 340 differs from ear-worn device 300 in that signal processing network precedes health network 306 in the signal processing chain.

Enhancing the audio signal with the signal processing network 312 prior to processing the audio signal with the health event network 306 may offer multiple advantages that aid in addressing the challenge of incorporating into a hearing aid audio-based health monitoring without compromising other important features, such as size and battery. In some embodiments, the signal processing network 312 is used to generate an output signal 341 having an improved signal-to-noise ratio (SNR). Accordingly, processing the signal 341 with the health event network 306 may be less computationally complex because the signal 341 is cleaner than signal 311.

Additionally, or alternatively, in some embodiments, the signal processing network 312 is used to estimate the SNR of the audio signal. In some embodiments, the SNR is provided back to the controller 304 and/or used by the signal processing network 312 to determine, based on the SNR, whether the audio signal is likely to include a health event sound, or some other sound. For example, speech may result in a relatively high SNR, while a health event may not. In some embodiments, if the SNR does not meet SNR criteria (e.g., it is outside the range of acceptable SNR), then the health event network 306 may be bypassed.

Additionally, or alternatively, in some embodiments, the signal processing network 312 may be used to differentiate between voices of different speakers. When the health event network 306 is used to monitor health events of the wearer of the ear-worn device, then the health event network 306 may be bypassed upon detecting sounds and/or voices that are not attributable to the wearer.

With reference to FIGS. 3A-3C, ear-worn devices 300, 320, and 340 may each include a single ear-piece having a microphone. In other examples, ear-worn devices 300, 320, and 340 may each be binaural and include two ear-pieces, each ear-piece having a respective microphone. Similarly, ear-worn devices 300, 320, and 340 may each include one or more output signal generators respectively included in one or two ear-pieces.

Figure 4:
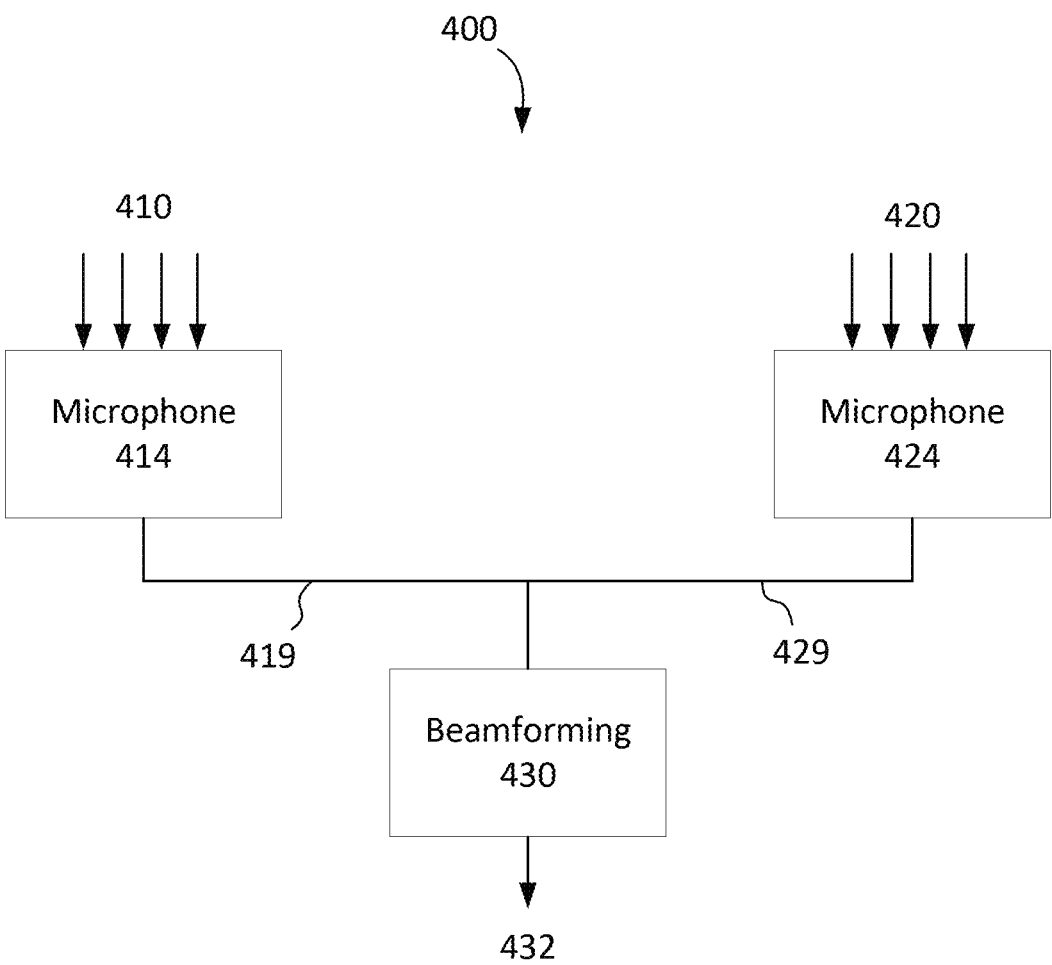
FIG. 4 illustrates example components of an ear-worn device having two microphones, according to a non-limiting embodiment of the present application.

FIG. 4 illustrates example components of an ear-worn device having two microphones, according to a non-limiting embodiment of the present application. FIG. 4 includes a portion of a circuitry 400 in an example ear-worn device. In some embodiments, the portion of circuitry 400 may be implemented in ear-worn device 102 (in FIG. 1), 202 (in FIG. 2), 300 (in FIG. 3A), 320 (in FIG. 3B), and 340 (in FIG. 3C), where the ear-worn device is binaural.

In FIG. 4, circuitry 400 may include a beamformer 430 configured to process audio signal 419, 429 respectively detected from microphones 414 and 424. In some embodiments, both microphones 414, 424 reside in one ear-piece of the ear-worn device. In some embodiments, the microphones 414, 424 respectively reside in one of two ear-pieces of the ear-worn device. For example, microphone 414 may reside in a left ear-piece, while microphone 424 may reside in a right ear-piece. It should be appreciated, however, that the ear-worn device may include one or more additional microphones residing on one or both ear-pieces, as aspects of the technology described herein are not limited in this respect.

In some embodiments, beamformer 430 may be implemented in controller 304 of FIGS. 3A-3C. Beamformer 430 may generate an enhanced audio signal 432 that accounts for sounds from different directions as detected by microphones 414 and 424. As described above, the audio signals 419, 429 respectively detected by the microphones 414 and 424 may be digital signals. The output from the beamformer 430 may be digital signal as well. The enhanced audio signal 432 may be provided to a neural network engine (NNE) and/or a digital signal processor (DSP) in the ear worn device. In some embodiments, the NNE and DSP are examples of signal processing network 312 and DSP 314 described with respect to FIGS. 3A-3C. The output of the NNE and/or DSP may be provided to the receivers of two ear-pieces.

In some embodiments, each ear-piece may be configured to communicate with the other ear-piece and exchange audio signal with the other ear-piece. For example, beamformer 430 may be residing in a first ear-piece of an ear-worn device. The audio signal detected by the microphone of the other ear-piece may be transferred from the other ear-piece to the ear-piece in which the beamformer 430 is residing. The output of the NNE (e.g., signal processing network 312 in FIGS. 3A-3C), or the output of the DSP (e.g., 314 in FIGS. 3A-3C) may be transferred back to the other ear-piece. It is appreciated that the two ear-pieces may be configured to communicate using any suitable protocol, such as near-field magnetic induction (NFMI) protocol, which allows for fast data exchange over short distances. Further, beamformer 430 may be optional, where a binaural audio stream may be detected from microphones 414 and 424 and provided to the NNE and/or DSP without using a beam-former.

In some embodiments, a health event network, such as health event network 306 in FIGS. 3A and 3C and health event and signal processing network 326 in FIG. 3B, is trained as a single network to extract and characterize health events. Such a network may process detected audio data, identify health events, and/or characterize health events. For example, a single network may be trained to both detect the occurrence of a cough and to characterize that cough. Characterizing the cough may include distinguishing between a cough of the wearer and the cough of another person. Additionally, or alternatively, characterizing a cough may include determining whether the cough is a wet cough or determining whether a cough is a dry cough. Such an implementation may be preferable where there are few battery and computation limitations.

In additional, or alternative embodiments, a health event network, may be implemented as more than one network. For example, to improve efficiency of operating an ear-worn device, the health event network may be implemented as a health event detector network and a health event character-ization network. In some embodiments, the health event detector network is a smaller network used to monitor audio data to identify the occurrence of health event(s). The health event detector network may serve as another controller, or be embedded in an existing controller, such as controller 304 in FIGS. 3A-3C. Once a health event has been identified, the health characterization network is used analyze the audio data corresponding to a health event to further characterize and/or classify the health event. Accordingly, the health event characterization network only processes the audio data that has been identified as corresponding to a health event, as opposed to processing all detected audio data. Such an implementation may help to reduce computational costs and conserve battery, allowing for prolonged use of the ear-worn device.

Figure 5A:
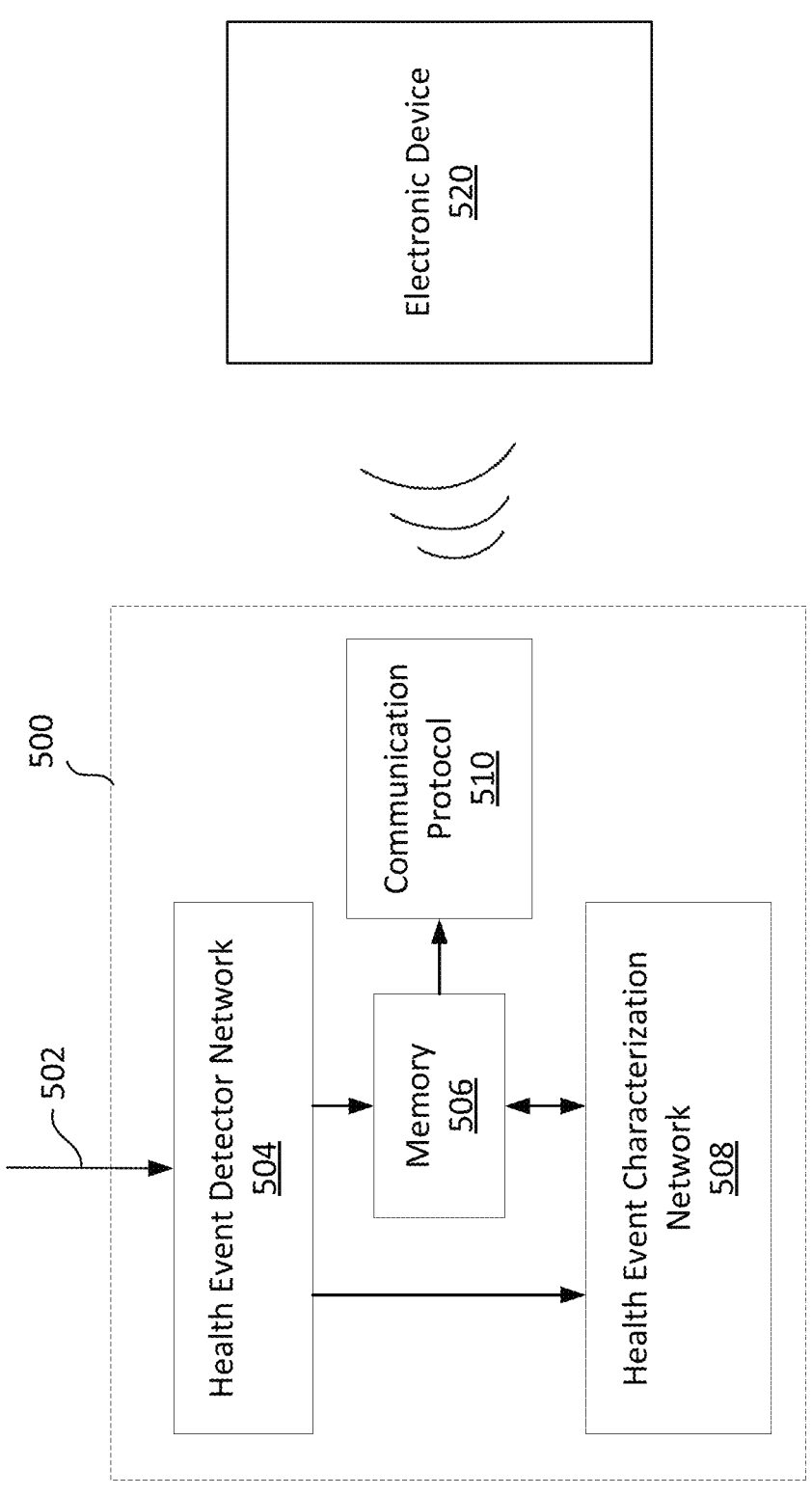
FIG. 5A illustrates an example circuit including a health event detector network and a health event characterization network implemented on an ear-worn device, according to a non-limiting embodiment of the present application.

FIG. 5A illustrates an example circuit including a health event detector network and a health event characterization network implemented on an ear-worn device, according to a non-limiting embodiment of the present application. The illustrated circuit 500 includes health event detector network 504, memory 506, health event characterization network 508, and a communication protocol circuit 510. The circuit 500 communicates with an external electronic device 520.

The health event detector network 504 operates on an incoming audio signal 502 to detect a health event reflected by the incoming audio signal. The health event detector network 504 includes any suitable circuitry for doing so, such as filters, amplifiers, signal converters (e.g., analog-to-digital converters) and processors. The incoming audio signal 502 may be any of the types of detected audio signals described herein, such as speech and/or environment noise. The health event detector network 504 includes suitable circuitry for processing such audio signals. In at least some embodiments, the health event detector network operates a machine learning model which analyzes the incoming audio signal 502 to detect characteristics of the incoming audio signal 502 reflecting a health event of the types described herein. Detection of health events is described further below in connection with FIG. 7, some of the functions of which may be performed by the health event detector network 504.

The health event characterization network 508 receives the output from the health event detector network 504 and processes the output to characterize the health event reflected by the incoming audio signal. For example, if the health event detector network 504 detects that the incoming audio signal 502 or a component of that signal represents a cough, the health event characterization network 508 may characterize the nature of the cough (e.g., wet cough) and/or a more general health event based on the cough, such as a respiratory infection. In at least some embodiments, the health event characterization network 508 operates a machine learning model which analyzes the signal provided by the health event detector network 504 to characterize the health event. Characterization of health events is described further below in connection with FIG. 7, some of the functions of which may be performed by the health event detector network 504.

The memory 506 is coupled to and communicates with the health event detector network 504 and health event characterization network 508. The memory 506 may stored data provided by one or both networks. For example, the memory may store the detected health event output from the health event detector network 504 and/or a characterization of the health event provided by the health event characterization network 508. The memory may provide data to the health event characterization network 508 to facilitate the characterization performed by the health event characterization network 508.

The communication protocol circuit 510 controls communication between the circuit 500 and the external electronic device 520. The circuit 500 may be implemented on an ear-worn device, such as a hearing aid, and the electronic device 520 may be any of the types described previously in connection with electronic devices 110 and 204. The two may communicate using any suitable wired or wireless communication protocol, governed by the communication protocol circuit 510.

Figure 5B:
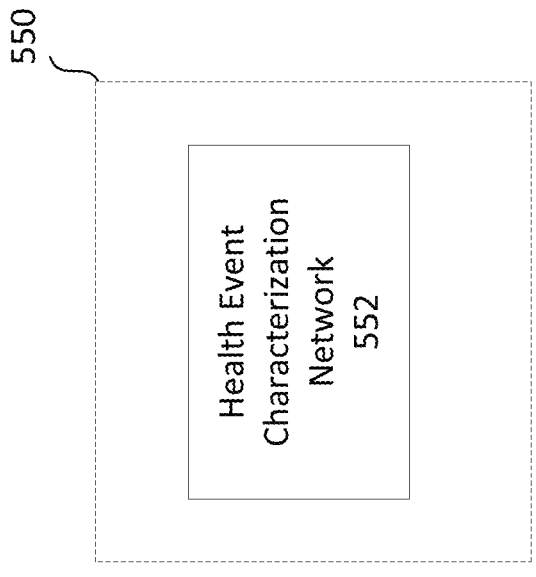
FIG. 5B illustrates a variation of the example circuit of FIG. 5A that may include the health event detector network implemented on the ear-worn device and the health event characterization network implemented on an electronic device, according to a non-limiting embodiment of the present application.
Figure 5B:
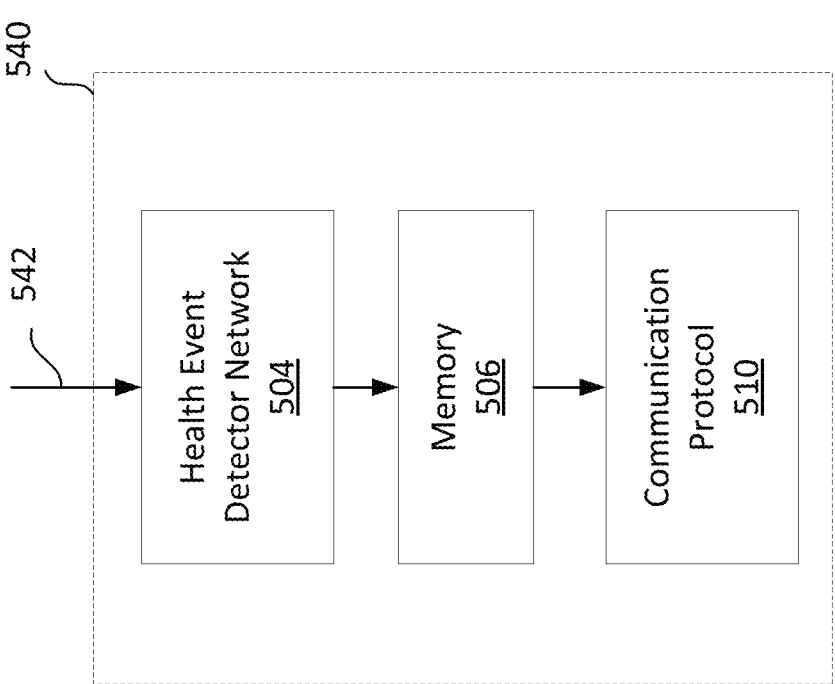

FIG. 5B illustrates a variation of the example circuit of FIG. 5A that may include the health event detector network implemented on the ear-worn device and the health event characterization network implemented on an electronic device, according to a non-limiting embodiment of the present application. The circuit 540, which may be on an ear-worn device of the types described herein, includes the health event detector network 504, memory 506, and communication protocol circuit 510, all described previously in connection with FIG. 5A. The illustrated system also includes an external electronic device 550 which includes a health event characterization network 552. The electronic device 550 may be any of the types described previously herein, and the health event characterization network 552 may operate in the manner described previously in connection with health event characterization network 508 of FIG. 5A. The difference is that in the example of FIG. 5B, the health event characterization network 552 receives signals, such as the output of health event detector network 504 (via the communication protocol circuit 510), from the ear-worn device.

The different locations of the health event characterization network 508 and 552 may allow for different designs tailored to the characteristics of the devices on which they are located. The health event characterization network 508 may be sized and structured to accommodate its inclusion on the ear-worn device, while the health event characterization network 552 may be sized and structured to take advantage of the larger space and processing power associated with an external electronic device such as a smartphone. In some embodiments, when the health event characterization network 508 is on the same device (e.g., the ear-worn device) as the health event detector network 504, those two networks may use the same ML model, or sub-models representing portions of the same ML model. In the embodiment of FIG. 5B, the health event characterization network 552 may use a ML model tailored to operation on a separate electronic device, and therefore distinct from any ML model used by the health event detector network 504.

In some embodiments, health event detector network 504 may be trained to predict, based on a segment of audio data, whether the segment of audio data includes a component attributable to a health event. This may include distinguishing between different sources of sound, such as background noise, speech, and/or health events. In some embodiments, health event characterization network 552 may be trained to process a segment of audio data, which includes a component attributable to a health event, to characterize the health event. For example, the health event characterization network 552 may be trained to distinguish between different types of health events. As an additional, or alternative example, the health event characterization network 552 may be trained to distinguish between different types of coughs, such as wet coughs and dry coughs. In some embodiments, the health event characterization network 552 may be larger and/or more complex that the health event detector network 504.

Figure 6:
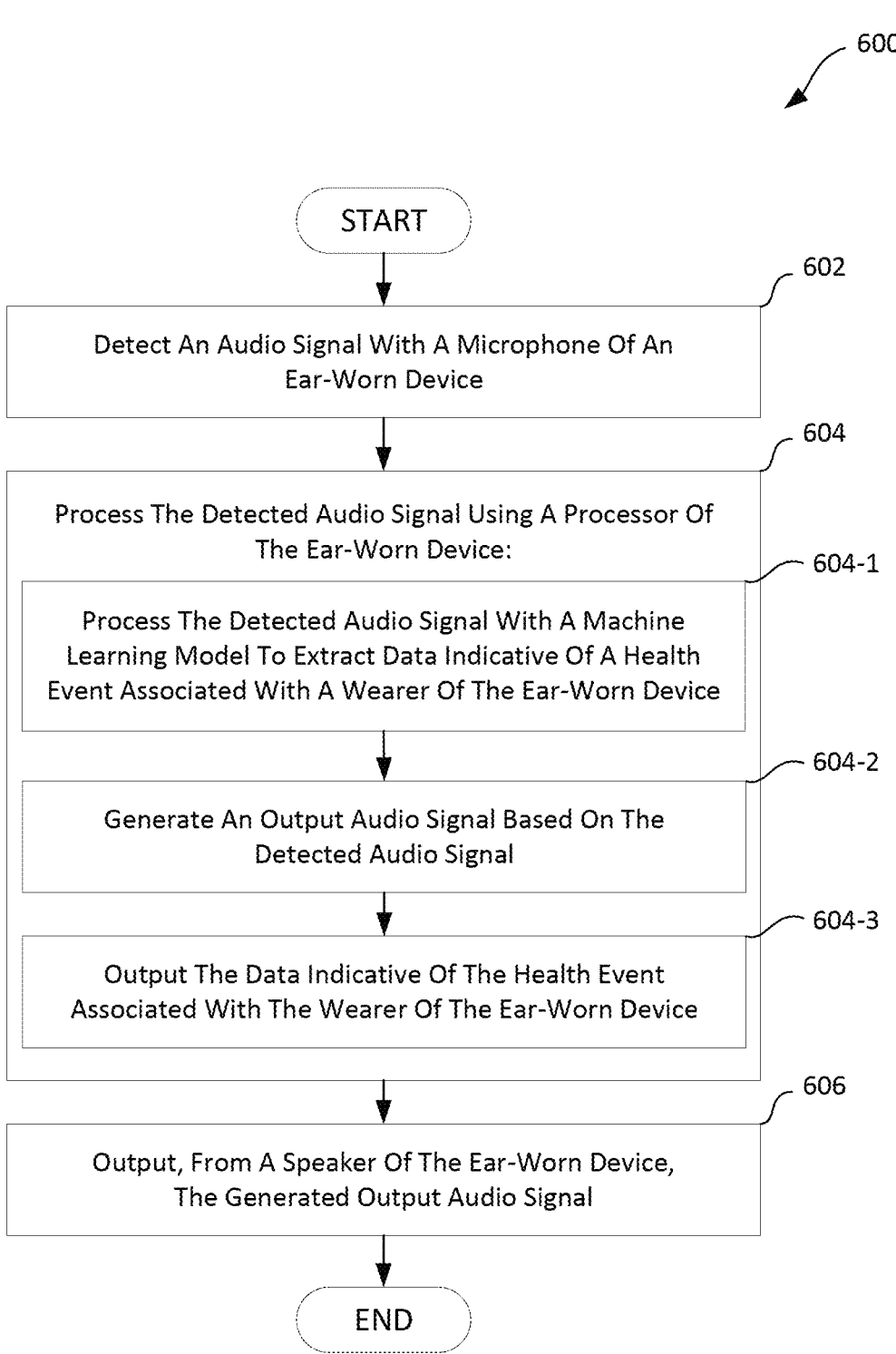
FIG. 6 is a flowchart of an example method of monitoring health of a wearer of an ear-worn device based on an audio signal detected by the ear-worn device, according to a non-limiting embodiment of the present application.

FIG. 6 is a flowchart of an example method of monitoring health of a wearer of an ear-worn device based on an audio signal detected by the ear-worn device, according to a non-limiting embodiment of the present application. The method 600 of FIG. 6 may be performed by the hearing systems (e.g., ear-worn devices) described herein.

The method 600 begins at stage 602 with detecting an audio signal with a microphone of an ear-worn device. The ear-worn device may be one of the types described herein, such as ear-worn 102 or 202.

At stage 604, the detected audio signal may be processed using a processor of the ear-worn device. The processing may involve one or more sub-stages. In the illustrated example, at sub-stage 604-1 the method comprises processing the detected audio signal with a machine learning model to extract data indicative of a health event associated with a wearer of the ear-worn device. This can be done in the manner previously described in connection with FIGS. 5A-5B.

At sub-stage 604-2 the method 600 comprises generating an output audio signal based on the detected audio signal. For example, the output audio signal may be of the type(s) described previously as being output by output signal generators 316.

At sub-stage 604-3, the method 600 comprises output the data indicative of the health event associated with the wearer of the ear-worn device. This may be done, for example, in the manner described previously in connection with FIGS. 5A-5A, and also communication protocol circuit 310.

The method comprises, at stage 606, outputting, from a speaker of the ear-worn device, the generated output audio signal.

The stages of method 600 may be performed in an order other than that shown. For example, the sub-stages 604-1, 604-2, 604-3 may be ordered differently or be performed in parallel.

Figure 7:
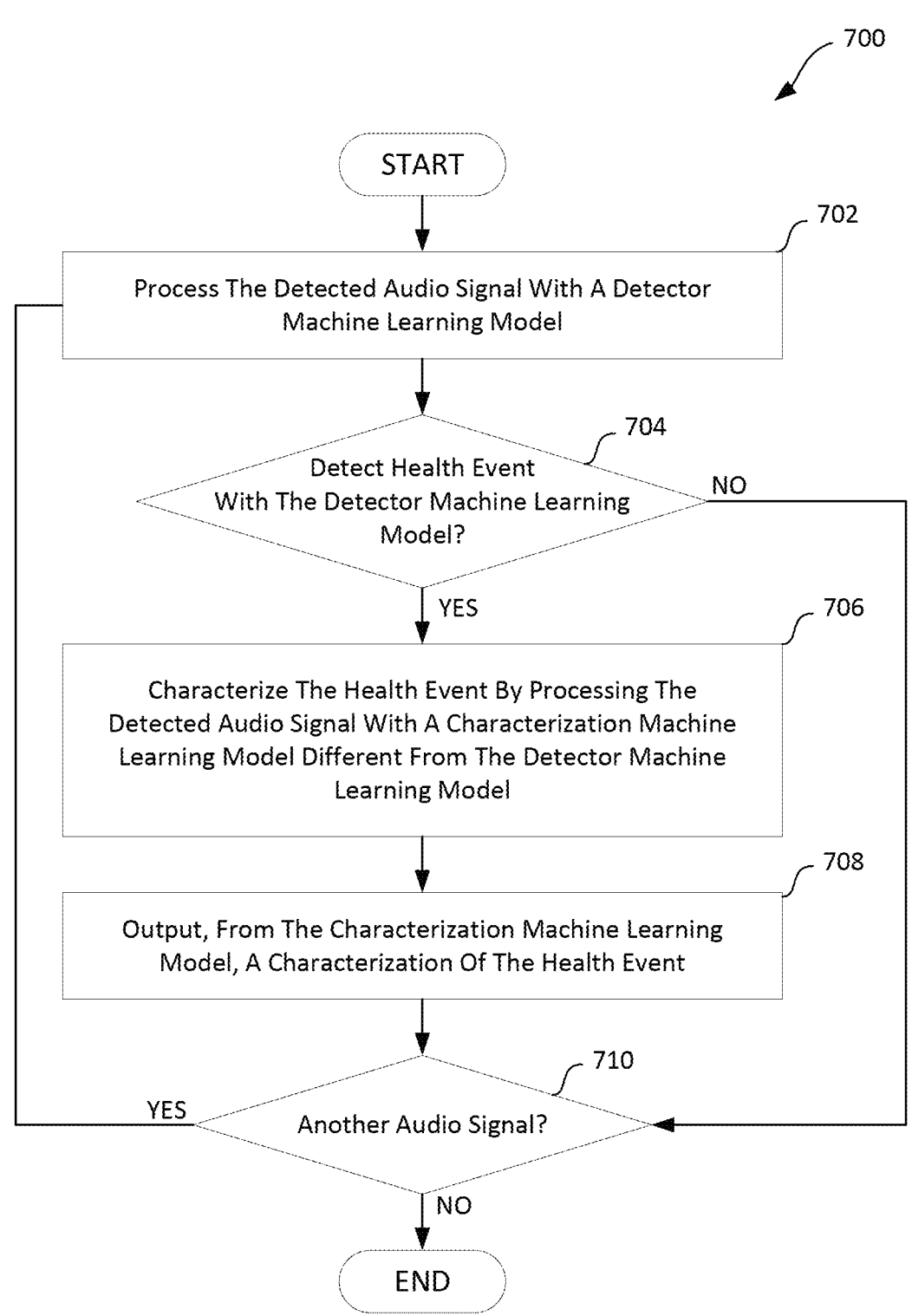
FIG. 7 is a flowchart of an example method of detecting and characterizing health events, according to a non-limiting embodiment of the present application.

FIG. 7 is a flowchart of an example method of detecting and characterizing health events, according to a non-limiting embodiment of the present application. The illustrated method is an example of the operation of the circuits illustrated in FIGS. 5A-5B. However, other circuit configurations may perform the illustrated method.

The method 700 begins at stage 702 with processing the detected audio signal with a detector machine learning model. Then, at stage 704 a determination may be made as to whether a health event was detected. If the answer is "Yes" then the method proceeds to stage 706. If the answer is "No" then the method proceeds to stage 710, described further below. The stages 702 and 704 may be performed by a health event detector, such as the health event detector network 504 of FIGS. 5A-5B.

At stage 706, the method comprises characterizing the health event by processing the detected audio signal with a characterization machine learning model. The characterization machine learning model may be different from the detector machine learning model used at stage 702. Alternatively, a single machine learning model may be trained to perform the tasks of both the detector and characterization machine learning model. At stage 708, the method comprises outputting, from the characterization machine learning model, a characterization of the health event. Stages 706 and 708 may be performed, for example, by the health event characterization network 508 or health event characterization network 552 described in connection with FIGS. 5A-5B, respectively.

After stage 708 is performed, the method determines, as stage 710, whether there is another audio signal received. If there is another audio signal received ("Yes"), the method returns to stage 702. If there is no further audio signal received ("No") the method ends. Also, if the answer is "No" at stage 704, then the method proceeds to stage 710.

Figure 8:
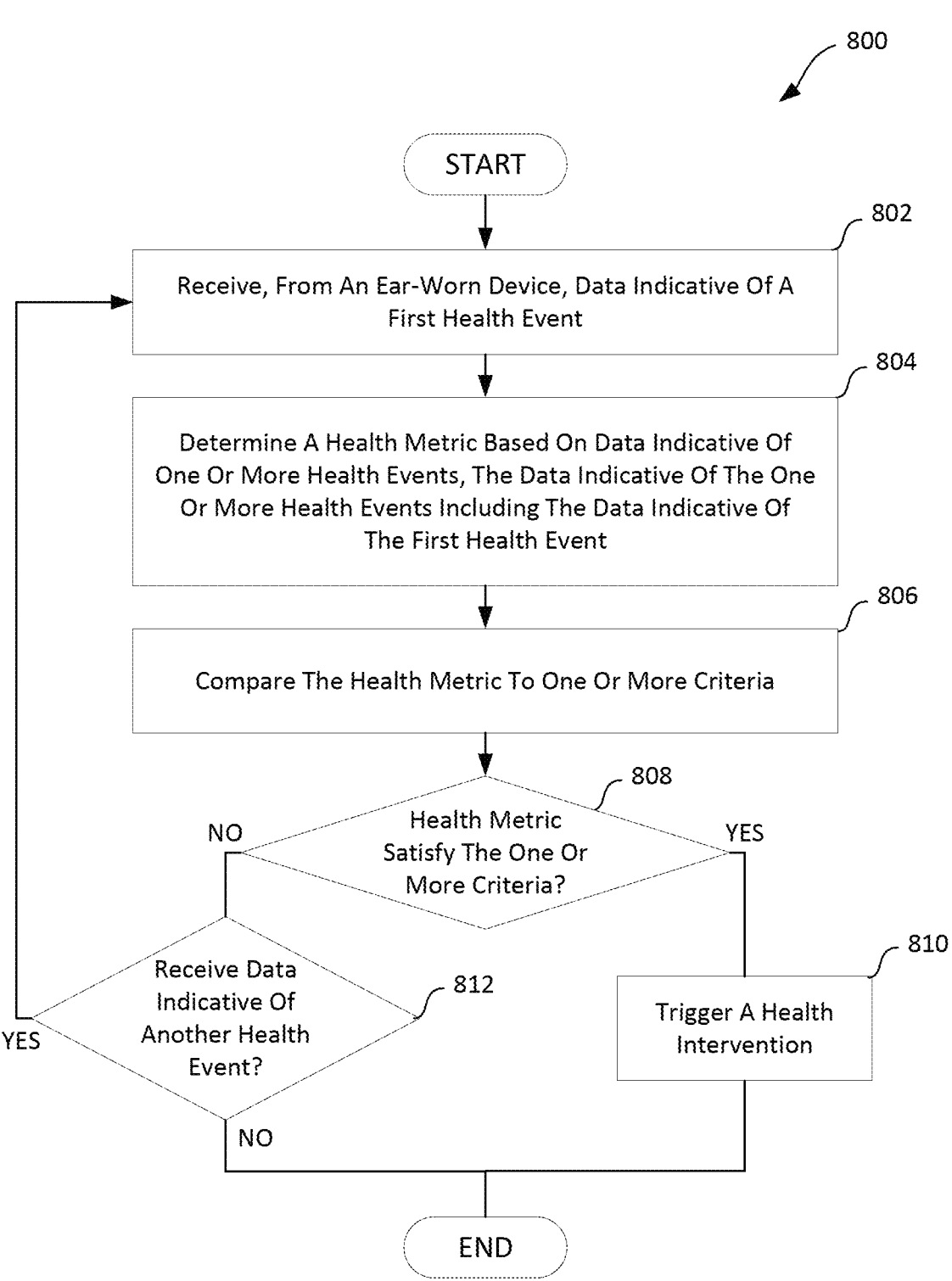
FIG. 8 is a flowchart of an example method of determining whether to trigger a health intervention, according to a non-limiting embodiment of the present application.

FIG. 8 is a flowchart of an example method of determining whether to trigger a health intervention, according to a non-limiting embodiment of the present application. The method 800 begins at stage 802 with receiving, from an ear-worn device, data indicative of a first health event. The data indicative of the first health event may be data indicative of a cough, sneeze, burp or other audible health event. The data may be received by an electronic device, such as electronic device 110, electronic device 206, or the other electronic devices described herein. The data may be received by a device near the ear-worn device (e.g., the wearer's smartphone) or by a device at a remote location, such as at a doctor's office.

At stage 804, the method comprises determining a health metric based on data indicative of one or more health events. The data indicative of the one or more health events includes the data indicative of the first health event. The health metric may take one of various forms, for instance being a score, a series of values, or a characterization such as "good," "clear", or "concerning".

At stage 806, the health metric determined from stage 804 may be compared to one or more criteria. For example, when the health metric is a numerical value, it may be compared to a reference value. The numerical value may represent the frequency of the health event, the duration of the health event, the strength of the health event, or the quality of the health event, as non-limiting example. Thus, the value representing the health metric may be compared to reference values of those types.

At stage 808 a determination is made based on the comparison of stage 806 as to whether the health metric satisfies the one or more criteria. If "Yes" then the method proceeds to stage 810 at which a health intervention is triggered, after which the method ends. If "No" then the method proceeds to stage 812 at which a determination is made as to whether newly received data (different than the data received at stage 802) is indicative of a health event. If "Yes" then the method returns to stage 802. If "No" then the method ends.

Stage 810 may trigger the health intervention in various ways, and the health intervention itself may take various forms. For example, stage 810 may trigger the health intervention by generating and sending a notification to a healthcare professional. Additionally, or alternatively, stage 810 may generate and send a notification to the wearer of the ear-worn device directing the wearer to contact a healthcare professional. Either type of notification may take the form of an electronic mail ("email") message, a phone call, or entry made in an application executing on a computing device, as non-limiting examples. The intervention itself may take the form a phone call from a healthcare professional, scheduling of an appointment, filling of a prescription, generation of medical instructions, or provision of a treatment program, as non-limiting examples. In some embodiments, the wearer may be able to view the data that triggered the notification in a smartphone application ("app").

Figure 9:
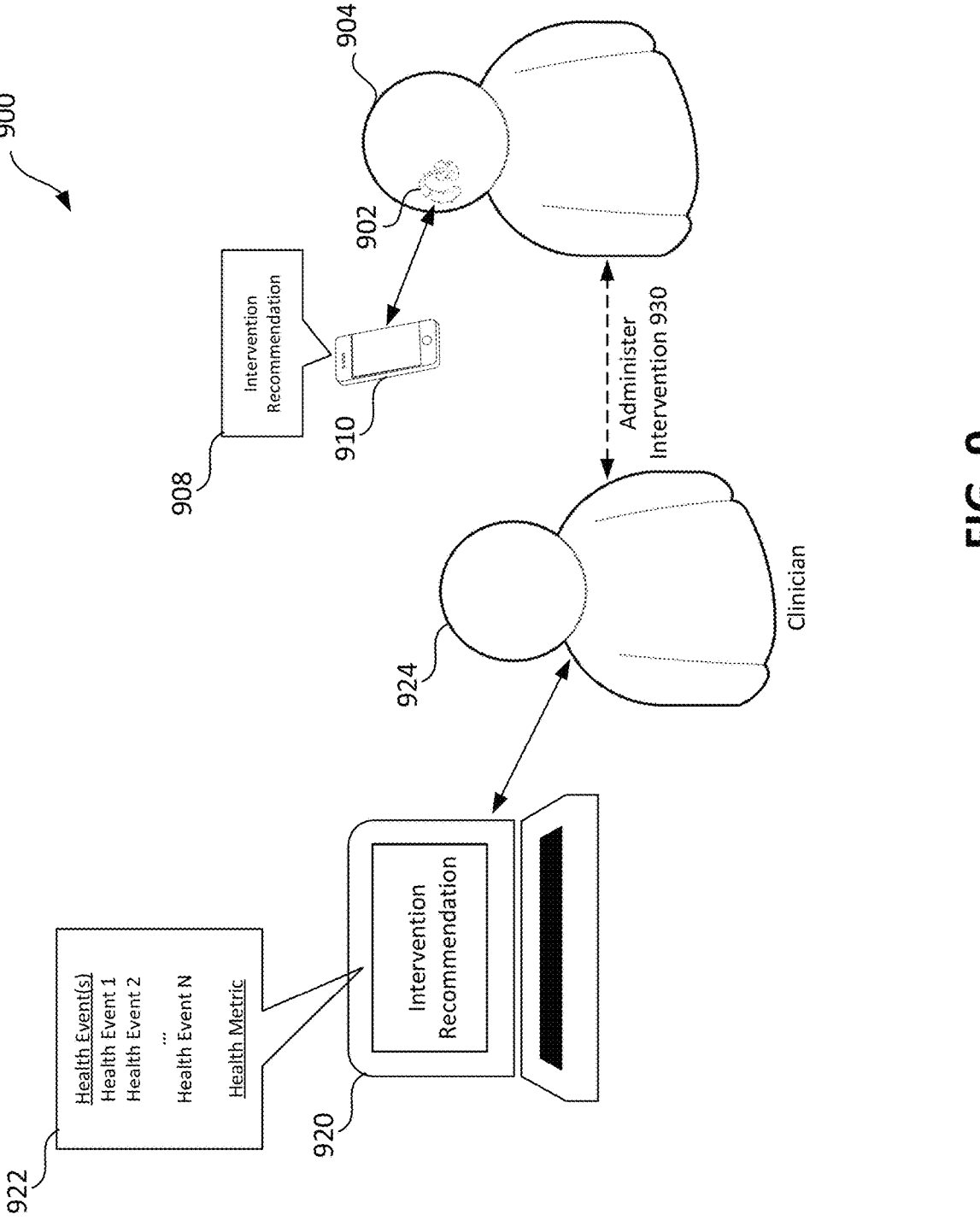
FIG. 9 illustrates an example of triggering a health intervention based on data indicative of one or more health events.

FIG. 9 illustrates an example of triggering a health intervention based on data indicative of one or more health events. The system 900 includes the wearer 904 of an ear-worn device 902. The wearer 904 has an electronic device 910, which may be any of the types described herein in connection with electronic device 100, electronic device 206, electronic device 520, and electronic device 550. For example, the electronic device 910 may be a smartphone. The system further includes a clinician 924 having a computing device 920.

The ear-worn device 902 may operate in the manner described previously herein for other ear-worn devices. For example, the ear-worn device 902 may receive audio signals such as sounds from the environment of wearer 904 and process the audio signal to produce an enhanced audio signal for output to the wearer 904. The ear-worn device 902 may also process the received audio signal on its own or in combination with electronic device 910 to detect a health event of any of the types described previously herein.

The electronic device 910 and/or the computing device 920 may then perform a method to determine whether to trigger a health intervention. For example, the electronic device 910 and/or the computing device 920 may perform the method 800 of FIG. 8. The computing device 920 may store or otherwise include a list 922 of health events (Health Event 1, Health Event 2 . . . Health Event N) and health metrics. One or more of the health events may be compared to the health metrics in the manner described in connection with method 800. As a result, an intervention recommendation 908 may be provided on the electronic device 910, for example on a display screen of the electronic device, and/or on the computing device 920. The clinician 924 may then administer intervention 930. The intervention may be any of the types described previously.

In some variations of the technology described herein, to reduce the power draw, the signal processing compute is interleaved with the health monitoring compute. This is achieved by having many processors distributed across the chip. One advantage of this is that each of the signal processing compute and the health monitoring compute can run at a relatively low clock speed. This is a more efficient way to do a computation than running the processor at a higher clock frequency because the power is proportionate to the square of the voltage. With enough processors, a second neural network, such as the health event neural network, can be computed at a lower frequency in between the layer computations of the primary network (e.g., the signal processing neural network) without sacrificing real-time processing. Such an embodiment aids in incorporating audio monitoring into a hearing aid without compromising other important features, such as size and battery.

In some variations of the technology described herein, a hearing aid configured for health monitoring may be used in conjunction with other sensors. For example, the hearing aid may classify a noise as a fall (e.g., the wearer fell). The fall may be confirmed based on accelerometer data collected during that time. Additionally, or alternatively, over time, the hearing aid may characterize the wearer's coughs. If the coughs are characterized as worsening over time, the presence of illness may be confirmed based on an elevated temperature detected by a thermometer and/or an elevated heart rate detected by a heart rate monitor.

In some variations of the technology described herein, the health monitoring techniques may be used to monitor the tenor of a speaker's voice. The tenor may be used as a biomarker for a state of mind and may be used to detect conditions like depression or anxiety. In some embodiments, other metadata relating to the wearer's communication might include the number of words used or the number of speakers spoken to. Such data may be used to determine an amount of socialization, or the number of unique words, which might be used to track cognitive function or mental acuity. A steep decline in either could be a useful indication in a decline in health.

Figure 10:
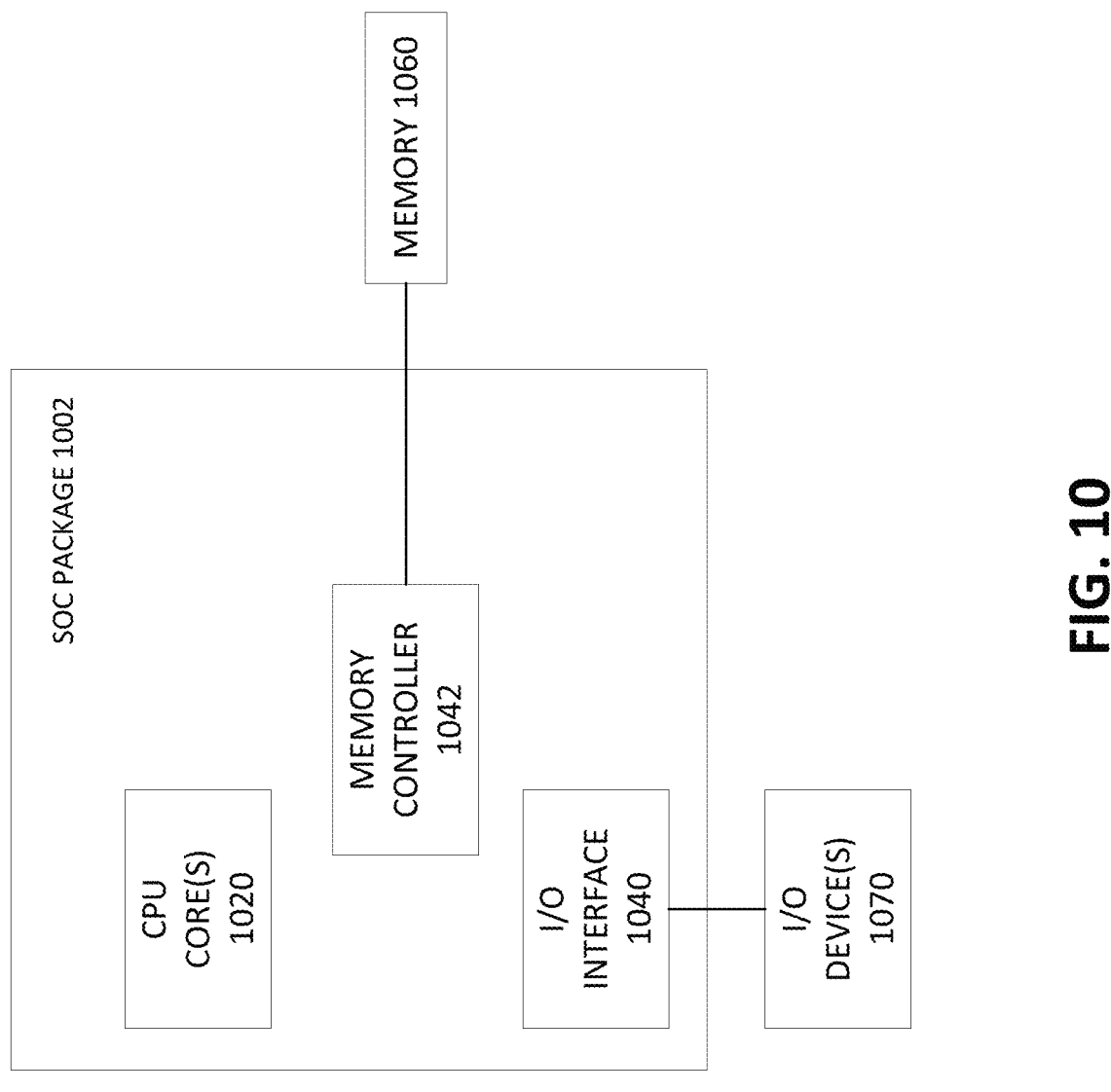
FIG. 10 illustrates a block diagram of a system-on-chip (SOC) package that may be implemented in an ear-worn device, according to a non-limiting embodiment of the present application.

FIG. 10 illustrates a block diagram of a system-on-chip (SOC) package that may be implemented in an ear-worn device, according to a non-limiting embodiment of the present application. In some embodiments, SOC package 1002 may implement various operations in an ear-worn device, such as 102 (in FIG. 1), 202 (in FIG. 2), 300 (in FIG. 3A), 320 (in FIG. 3B), 340 (in FIG. 3C) or a circuitry of an ear-worn device such as 400 (in FIG. 4). In various embodiments, SOC 1002 includes one or more Central Processing Unit (CPU) cores 1020, an Input/Output (I/O) interface 1040, and a memory controller 1042. Various components of the SOC package 1002 may be optionally coupled to an interconnect or bus such as discussed herein with reference to the other figures. Also, the SOC package 1002 may include components such as those discussed with reference to the ear-worn device described in FIGS. 1-9. Further, each component of the SOC package 1020 may include one or more other components of the ear-worn device, e.g., as discussed with reference to FIGS. 3A-4. In one embodiment, SOC package 1002 (and its components) is provided on one or more Integrated Circuit (IC) die, e.g., which are packaged into a single semiconductor device. The single semiconductor device may be configured to be used as an ear-worn device, an amplification system or a hearing device to be used in the human ear canal.

As illustrated in FIG. 10, SOC package 1002 is coupled to a memory 1060 via the memory controller 1042. In an embodiment, the memory 1060 (or a portion of it) can be integrated on the SOC package 1002. The T/O interface 1040 may be coupled to one or more I/O devices 1070, e.g., via an interconnect and/or bus such as discussed herein. I/O device(s) 1070 may include interfaces to communicate with SOC 1002. In an exemplary embodiment, I/O interface 1040 communicates wirelessly with I/O device 1070. SOC package 1002 may comprise hardware, software and logic to implement, for example, the various components or methods described in FIGS. 1-9. The implementation may be communicated with an auxiliary device, e.g., I/O device 1070. I/O device 1070 may comprise additional communication capabilities, e.g., cellular, BlueTooth, WiFi or other protocols, to access any component in the ear-worn device.

Figure 11:
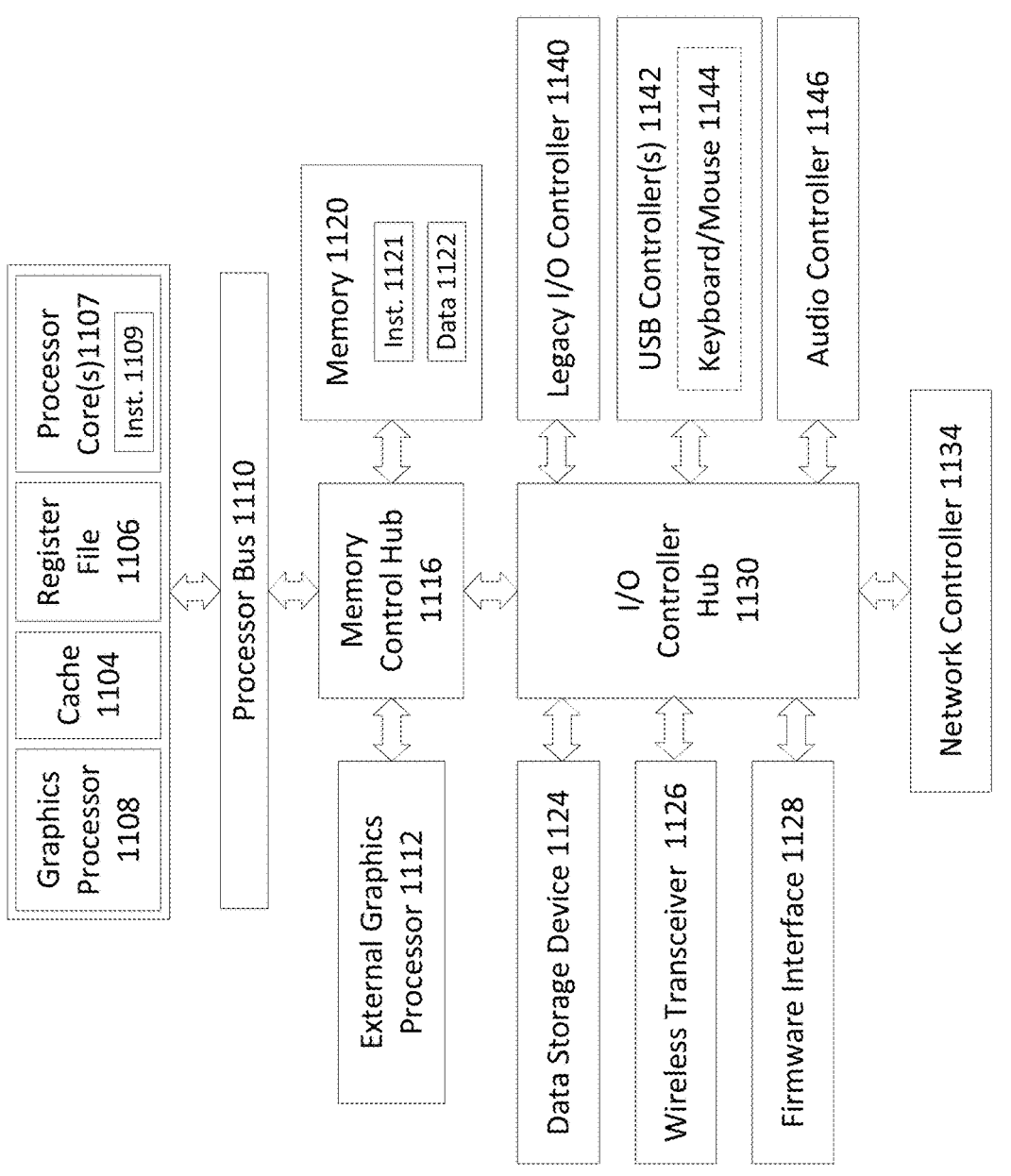
FIG. 11 illustrates an example of a computing system that may be implemented in an electronic device to implement various embodiments described in the present application.

FIG. 11 illustrates an example of a computing system that may be implemented in an electronic device to implement various embodiments described in the present application. In some embodiments, system 1100 may implement operations described in various embodiments with reference to FIGS. 1-2 and 8-9 on an electronic device, such as 110 (in FIG. 1) or 204 (in FIG. 2). In some embodiments, the system 1100 includes one or more processors 1102 and one or more graphics processors 1108, and may be a single processor desktop system, a multiprocessor workstation system, or a server system having a large number of processors 1102 or processor cores 1107. In on embodiment, the system 1100 is a processing platform incorporated within a system-on-a-chip (SoC or SOC) integrated circuit for use in mobile, handheld, or embedded devices.

An embodiment of system 1100 can include or be incorporated within a server-based smart-device platform or an online server with access to the internet. In some embodiments system 1100 is a mobile phone, smart phone, tablet computing device or mobile Internet device. Data processing system 1100 can also include, couple with, or be integrated within a wearable device, such as a smart watch wearable device, smart eyewear device (e.g., face-worn glasses), augmented reality device, or virtual reality device. In some embodiments, data processing system 1100 is a television or set top box device having one or more processors 1102 and a graphical interface generated by one or more graphics processors 1108.

In some embodiments, the one or more processors 1102 each include one or more processor cores 1107 to process instructions which, when executed, perform operations for system and user software. In some embodiments, each of the one or more processor cores 1107 is configured to process a specific instruction set 1109. In some embodiments, instruction set 1109 may facilitate Complex Instruction Set Computing (CISC), Reduced Instruction Set Computing (RISC), or computing via a Very Long Instruction Word (VLIW). Multiple processor cores 1107 may each process a different instruction set 1109, which may include instructions to facilitate the emulation of other instruction sets. Processor core 1107 may also include other processing devices, such as a DSP.

In some embodiments, the processor 1102 includes cache memory 1104. Depending on the architecture, the processor 1102 can have a single internal cache or multiple levels of internal cache. In some embodiments, the cache memory is shared among various components of the processor 1102. In some embodiments, the processor 1102 also uses an external cache (e.g., a Level-3 (L3) cache or Last Level Cache (LLC)) (not shown), which may be shared among processor cores 1107 using known cache coherency techniques. A register file 1106 is additionally included in processor 1102 which may include different types of registers for storing different types of data (e.g., integer registers, floating point registers, status registers, and an instruction pointer register). Some registers may be general-purpose registers, while other registers may be specific to the design of the processor 1102.

In some embodiments, processor 1102 is coupled to a processor bus 1110 to transmit communication signals such as address, data, or control signals between processor 1102 and other components in system 1100. In one embodiment the system 1100 uses an exemplary 'hub' system architecture, including a memory controller hub 1116 and an Input Output (I/O) controller hub 1130. A memory controller hub 1116 facilitates communication between a memory device and other components of system 1100, while an I/O Controller Hub (ICH) 1130 provides connections to I/O devices via a local I/O bus. In one embodiment, the logic of the memory controller hub 1116 is integrated within the processor.

Memory device 1120 can be a dynamic random-access memory (DRAM) device, a static random access memory (SRAM) device, flash memory device, phase-change memory device, or some other memory device having suitable performance to serve as process memory. In one embodiment the memory device 1120 can operate as system memory for the system 1100, to store data 1122 and instructions 1121 for use when the one or more processors 1102 executes an application or process. Memory controller hub 1116 also couples with an optional external graphics processor 1112, which may communicate with the one or more graphics processors 1108 in processors 1102 to perform graphics and media operations.

In some embodiments, ICH 1130 enables peripherals to connect to memory device 1120 and processor 1102 via a high-speed I/O bus. The I/O peripherals include, but are not limited to, an audio controller 1146, a firmware interface 1128, a wireless transceiver 1126 (e.g., Wi-Fi, Bluetooth), a data storage device 1124 (e.g., hard disk drive, flash memory, etc.), and a legacy I/O controller 1140 for coupling legacy (e.g., Personal System 2 (PS/2)) devices to the system. One or more Universal Serial Bus (USB) controllers 1142 connect input devices, such as keyboard and mouse 1144 combinations. A network controller 1134 may also couple to ICH 1130. In some embodiments, a high-performance network controller (not shown) couples to processor bus 1110. It will be appreciated that the system 1100 shown is exemplary and not limiting, as other types of data processing systems that are differently configured may also be used. For example, the I/O controller hub 1130 may be integrated within the one or more processor 1102, or the memory controller hub 1116 and I/O controller hub 1130 may be integrated into a discreet external graphics processor, such as the external graphics processor 1112.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. A method of monitoring health of a wearer of an ear-worn device based on an audio signal detected by the ear-worn device, the method comprising:
detecting the audio signal with a microphone of the ear-worn device;
processing the detected audio signal using a processor of the ear-worn device, the processing comprising:
extracting data indicative of a health event associated with the wearer of the ear-worn device by processing the detected audio signal with a machine learning model, wherein the machine learning model is configured to output a duration of the health event and/or a severity of the health event;
generating an output audio signal based on the detected audio signal; and
outputting the data indicative of the health event associated with the wearer of the ear-worn device; and
outputting, from an output signal generator of the ear-worn device, the generated output audio signal.

2. The method of claim 1, wherein the ear-worn device is a hearing aid.

3. The method of claim 1, wherein the health event comprises coughing, sneezing, wheezing, snoring, chewing, swallowing, drinking, and/or speaking.

4. The method of claim 1, wherein processing the detected audio signal with the machine learning model comprises processing the detected audio signal using a neural network.

5. The method of claim 4, wherein processing the detected audio signal with the machine learning model comprises processing the detected audio signal with a recurrent neural network or a convolutional neural network.

6. The method of claim 1, wherein processing the detected audio signal with the machine learning model comprises:
detecting the health event by processing the detected audio signal with a detector machine learning model; and after detecting the health event with the detector machine learning model, characterizing the health event by processing the detected audio signal with a characterization machine learning model, wherein the detector machine learning model is different from the characterization machine learning model.

7. The method of claim 6, wherein the characterization machine learning model is configured to output the duration of the health event and/or the severity of the health event.

8. The method of claim 1, wherein the extracted data indicative of the health event comprises a portion of the detected audio signal corresponding to the health event, an indication that the health event occurred, and/or a characterization of the health event.

9. The method of claim 1, wherein outputting the data indicative of the health event comprises storing the data indicative of the health event in a memory of the ear-worn device.

10. The method of claim 1, wherein outputting the data indicative of the health event comprises transmitting, to a computing device different from the ear-worn device, the data indicative of the health event.

11. The method of claim 10, wherein outputting the data indicative of the health event comprises transmitting the data indicative of the health event using a wireless communication protocol.

12. The method of claim 1, wherein generating the output audio signal based on the detected audio signal comprises removing background noise from the detected audio signal.

13. The method of claim 12, wherein removing the background noise from the detected audio signal comprises generating a processed audio signal, and
wherein processing the detected audio signal with the machine learning model comprises processing the processed audio signal with the machine learning model.

14. The method of claim 12, wherein generating the output audio signal based on the detected audio signal further comprises, after removing the background noise from the detected audio signal, amplifying at least one component of the detected audio signal.

15. The method of claim 1,
wherein generating the output audio signal based on the detected audio signal comprises estimating a signal-to-noise ratio (SNR) of the detected audio signal, and
wherein extracting the data indicative of the health event associated with the wearer of the ear-worn device comprises processing the detected audio signal with the machine learning model only when the estimated SNR is within a specified range.

16. The method of claim 1, wherein processing the detected audio signal with the machine learning model comprises processing the detected audio signal with a first machine learning model, and wherein generating the output audio signal based on the detected audio signal comprises:
isolating a component of the detected audio signal representing a voice of the wearer from among temporally overlapping voice components from multiple speakers by processing the detected audio signal with a second machine learning model using a voice signature of the wearer.

17. The method of claim 16, wherein processing the detected audio signal with the first machine learning model comprises processing only the isolated component of the detected audio signal with the first machine learning model.

18. The method of claim 1, wherein the machine learning model comprises a first machine learning model, and wherein generating the output audio signal comprises processing the detected audio signal with a second machine learning model.

19. The method of claim 18, wherein processing the detected audio signal with the second machine learning model comprises processing the detected audio signal with a neural network.

20. The method of claim 1, wherein processing the detected audio signal using the processor of the ear-worn device further comprises computing a Fast Fourier Transform (FFT) of the detected audio signal.

21. The method of claim 20, wherein computing the FFT of the detected audio signal comprises computing the FFT prior to:
extracting the data indicative of the health event associated with the wearer of the ear-worn device by processing the detected audio signal with the machine learning model; and
generating the output audio signal based on the detected audio signal.

22. An ear-worn device configured to monitor health of a wearer of the ear-worn device based on an audio signal detected by the ear-worn device, the ear-worn device comprising:
a microphone configured to detect the audio signal;
a processor;
at least one non-transitory computer-readable storage medium storing processor-executable instructions that, when executed by the processor, cause the processor to perform a method comprising:
extracting data indicative of a health event associated with the wearer of the ear-worn device by processing the detected audio signal with a machine learning model, wherein the machine learning model is configured to output a duration of the health event and/or a severity of the health event;
generating an output audio signal based on the detected audio signal; and
outputting the data indicative of the health event associated with the wearer of the ear-worn device; and
an output signal generator configured to output the generated output audio signal.

23. The ear-worn device of claim 22, wherein the ear-worn device is a hearing aid.

24. The ear-worn device of claim 22, wherein the health event comprises coughing, sneezing, wheezing, snoring, chewing, swallowing, and/or drinking.

25. The ear-worn device of claim 22, wherein processing the detected audio signal with the machine learning model comprises processing the detected audio signal using a neural network.

26. The ear-worn device of claim 25, wherein processing the detected audio signal with the machine learning model comprises processing the detected audio signal with a recurrent neural network or a convolutional neural network.

27. The ear-worn device of claim 22, wherein processing the detected audio signal with the machine learning model comprises:
detecting the health event by processing the detected audio signal with a detector machine learning model; and
after detecting the health event with the detector machine learning model, characterizing the health event by processing the detected audio signal with a characterization machine learning model, wherein the detector machine learning model is different from the characterization machine learning model.

28. The ear-worn device of claim 27, wherein the characterization machine learning model is configured to output the duration of the health event and/or the severity of the health event.

29. The ear-worn device of claim 22, wherein the extracted data indicative of the health event comprises a portion of the detected audio signal corresponding to the health event, an indication that the health event occurred, and/or a characterization of the health event.

30. The ear-worn device of claim 22, wherein outputting the data indicative of the health event comprises storing the data indicative of the health event in a memory of the ear-worn device.

31. The ear-worn device of claim 22, wherein outputting the data indicative of the health event comprises transmitting, to a computing device different from the ear-worn device, the data indicative of the health event.

32. The ear-worn device of claim 31, wherein outputting the data indicative of the health event comprises transmitting the data indicative of the health event using a wireless communication protocol.

33. The ear-worn device of claim 22, wherein generating the output audio signal based on the detected audio signal comprises removing background noise from the detected audio signal.

34. The ear-worn device of claim 33, wherein removing the background noise from the detected audio signal comprises generating a processed audio signal, and
wherein processing the detected audio signal with the machine learning model comprises processing the processed audio signal with the machine learning model.

35. The ear-worn device of claim 33, wherein generating the output audio signal based on the detected audio signal further comprises, after removing the background noise from the detected audio signal, amplifying at least one component of the detected audio signal.

36. The ear-worn device of claim 22,
wherein generating the output audio signal based on the detected audio signal comprises estimating a signal-to-noise ratio (SNR) of the detected audio signal, and
wherein extracting the data indicative of the health event associated with the wearer of the ear-worn device comprises processing the detected audio signal with the machine learning model only when the estimated SNR is within a specified range.

37. The ear-worn device of claim 22, wherein processing the detected audio signal with the machine learning model comprises processing the detected audio signal with a first machine learning model, and wherein generating the output audio signal based on the detected audio signal comprises:
isolating a component of the detected audio signal representing a voice of the wearer from among temporally overlapping voice components from multiple speakers by processing the detected audio signal with a second machine learning model using a voice signature of the wearer.

38. The ear-worn device of claim 37, wherein processing the detected audio signal with the first machine learning model to extract data indicative of the health event associated with the wearer of the ear-worn device comprises processing only the isolated component of the detected audio signal with the first machine learning model.

39. The ear-worn device of claim 22, wherein the machine learning model comprises a first machine learning model, and wherein generating the output audio signal comprises processing the detected audio signal with a second machine learning model.

40. The ear-worn device of claim 39, wherein processing the detected audio signal with the second machine learning model comprises processing the detected audio signal with a neural network.

41. The ear-worn device of claim 22, wherein the method further comprises computing a Fast Fourier Transform (FFT) of the detected audio signal.

42. The ear-worn device of claim 41, wherein computing the FFT of the detected audio signal comprises computing the FFT prior to:
extracting the data indicative of the health event associated with the wearer of the ear-worn device by processing the detected audio signal with the machine learning model; and
generating the output audio signal based on the detected audio signal.

43. At least one non-transitory computer-readable storage medium storing processor-executable instructions that, when executed by a processor, cause the processor to perform a method of monitoring health of a wearer of an ear-worn device based on an audio signal detected by the ear-worn device, the method comprising:
extracting data indicative of a health event associated with the wearer of the ear-worn device by processing the detected audio signal with a machine learning model, wherein the machine learning model is configured to output a duration of the health event and/or a severity of the health event;
generating an output audio signal based on the detected audio signal;
outputting the data indicative of the health event associated with the wearer of the ear-worn device; and
transmitting the output audio signal to an output signal generator of the ear-worn device.

44. The at least one non-transitory computer-readable storage medium of claim 43, wherein the ear-worn device is a hearing aid.

45. The at least one non-transitory computer-readable storage medium of claim 43, wherein the health event comprises coughing, sneezing, wheezing, snoring, chewing, swallowing, and/or drinking.

46. The at least one non-transitory computer-readable storage medium of claim 43, wherein processing the detected audio signal with the machine learning model comprises processing the detected audio signal using a neural network.

47. The at least one non-transitory computer-readable storage medium of claim 46, wherein processing the detected audio signal with the machine learning model comprises processing the detected audio signal with a recurrent neural network or a convolutional neural network.

48. The at least one non-transitory computer-readable storage medium of claim 43, wherein processing the detected audio signal with the machine learning model comprises:
detecting the health event by processing the detected audio signal with a detector machine learning model; and
after detecting the health event with the detector machine learning model, characterizing the health event by processing the detected audio signal with a characterization machine learning model, wherein the detector machine learning model is different from the characterization machine learning model.

49. The at least one non-transitory computer-readable storage medium of claim 48, wherein the characterization machine learning model is configured to output the duration of the health event and/or the severity of the health event.

50. The at least one non-transitory computer-readable storage medium of claim 43, wherein the extracted data indicative of the health event comprises a portion of the detected audio signal corresponding to the health event, an indication that the health event occurred, and/or a characterization of the health event.

51. The at least one non-transitory computer-readable storage medium of claim 43, wherein outputting the data indicative of the health event comprises storing the data indicative of the health event in a memory of the ear-worn device.

52. The at least one non-transitory computer-readable storage medium of claim 43, wherein outputting the data indicative of the health event comprises transmitting, to a computing device different from the ear-worn device, the data indicative of the health event.

53. The at least one non-transitory computer-readable storage medium of claim 52, wherein outputting the data indicative of the health event comprises transmitting the data indicative of the health event using a wireless communication protocol.

54. The at least one non-transitory computer-readable storage medium of claim 43, wherein generating the output audio signal based on the detected audio signal comprises removing background noise from the detected audio signal.

55. The at least one non-transitory computer-readable storage medium of claim 54, wherein removing the background noise from the detected audio signal comprises generating a processed audio signal, and wherein processing the detected audio signal with the machine learning model comprises processing the processed audio signal with the machine learning model.

56. The at least one non-transitory computer-readable storage medium of claim 54, wherein generating the output audio signal based on the detected audio signal further comprises, after removing the background noise from the detected audio signal, amplifying at least one component of the detected audio signal.

57. The at least one non-transitory computer-readable storage medium of claim 43, wherein generating the output audio signal based on the detected audio signal comprises estimating a signal-to-noise ratio (SNR) of the detected audio signal, and wherein extracting the data indicative of the health event associated with the wearer of the ear-worn device comprises processing the detected audio signal with the machine learning model only when the estimated SNR is within a specified range.

58. The at least one non-transitory computer-readable storage medium of claim 43, wherein processing the detected audio signal with the machine learning model comprises processing the detected audio signal with a first machine learning model, and wherein generating the output audio signal based on the detected audio signal comprises:

isolating a component of the detected audio signal representing a voice of the wearer from among temporally overlapping voice components from multiple speakers by processing the detected audio signal with a second machine learning model using a voice signature of the wearer.

59. The at least one non-transitory computer-readable storage medium of claim 58, wherein processing the detected audio signal with the first machine learning model to extract data indicative of the health event associated with the wearer of the ear-worn device comprises processing only the isolated component of the detected audio signal with the first machine learning model.

60. The at least one non-transitory computer-readable storage medium of claim 43, wherein the machine learning model comprises a first machine learning model, and wherein generating the output audio signal comprises processing the detected audio signal with a second machine learning model.

61. The at least one non-transitory computer-readable storage medium of claim 60, wherein processing the detected audio signal with the second machine learning model comprises processing the detected audio signal with a neural network.

62. The at least one non-transitory computer-readable storage medium of claim 43, the method further comprises computing a Fast Fourier Transform (FFT) of the detected audio signal.

63. The at least one non-transitory computer-readable storage medium of claim 62, wherein computing the FFT of the detected audio signal comprises computing the FFT prior to:

extracting the data indicative of the health event associated with the wearer of the ear-worn device by processing the detected audio signal with the machine learning model; and generating the output audio signal based on the detected audio signal.

64. The method of claim 1, wherein the machine learning model is further configured to output a type of the health event.

65. The ear-worn device of claim 22, wherein the machine learning model is further configured to output a type of the health event.

66. The at least one non-transitory computer-readable storage medium of claim 43, wherein the machine learning model is further configured to output a type of the health event.

* * * * *